US011413172B2

(12) United States Patent
Nagesh et al.

(10) Patent No.: US 11,413,172 B2
(45) Date of Patent: Aug. 16, 2022

(54) STENT ASSEMBLIES INCLUDING PASSAGES TO PROVIDE BLOOD FLOW TO CORONARY ARTERIES AND METHODS OF DELIVERING AND DEPLOYING SUCH STENT ASSEMBLIES

(71) Applicant: Medtronic, Inc., Minneapolis, MN (US)

(72) Inventors: Shishira Nagesh, San Francisco, CA (US); Paul Rothstein, Elk River, MN (US)

(73) Assignee: Medtronic, Inc., Minneapolis, MN (US)

( * ) Notice: Subject to any disclaimer, the term of this patent is extended or adjusted under 35 U.S.C. 154(b) by 376 days.

(21) Appl. No.: 16/358,072

(22) Filed: Mar. 19, 2019

(65) Prior Publication Data
US 2019/0209353 A1    Jul. 11, 2019

Related U.S. Application Data

(62) Division of application No. 14/841,749, filed on Sep. 1, 2015, now abandoned.

(51) Int. Cl.
*A61F 2/856* (2013.01)
*A61F 2/07* (2013.01)
(Continued)

(52) U.S. Cl.
CPC ................ *A61F 2/856* (2013.01); *A61F 2/07* (2013.01); *A61F 2/2418* (2013.01); *A61F 2/915* (2013.01);
(Continued)

(58) Field of Classification Search
CPC ........................... A61F 2/856; A61F 2002/061
See application file for complete search history.

(56) References Cited

U.S. PATENT DOCUMENTS 3,574,865 A    4/1971  Hamaker
3,671,979 A    6/1972  Moulopoulos
(Continued)

FOREIGN PATENT DOCUMENTS

CN    202207217        5/2012
CN    203029425 U      7/2013
(Continued)

OTHER PUBLICATIONS

PCT/US2014/058913, PCT International Search Report and the Written Opinion, dated Dec. 23, 2014.
(Continued)

*Primary Examiner* — Megan Y Wolf
(74) *Attorney, Agent, or Firm* — Medler Ferro Woodhouse & Mills PLLC

(57) ABSTRACT

An anchor stent assembly to be used with a valve component includes a generally tubular frame having a first end and a second end, the frame defining a central passage and a central axis. A secondary passage is defined between n inner surface of the frame and an outer surface of an inner rib disposed closer to the central axis than the frame. An extension tube is disposed through the secondary passage. The extension tube includes an extension tube lumen having a first opening at a first end of the extension tube and a second opening at a second end of the extension tube.

9 Claims, 28 Drawing Sheets

(51) Int. Cl.
*A61F 2/24* (2006.01)
*A61F 2/915* (2013.01)
*A61F 2/82* (2013.01)
*A61F 2/966* (2013.01)
*A61F 2/06* (2013.01)
*A61F 2/848* (2013.01)

(52) U.S. Cl.
CPC .............. *A61F 2/2436* (2013.01); *A61F 2/966* (2013.01); *A61F 2002/061* (2013.01); *A61F 2002/826* (2013.01); *A61F 2002/828* (2013.01); *A61F 2002/8486* (2013.01); *A61F 2002/91533* (2013.01); *A61F 2002/91575* (2013.01); *A61F 2002/91583* (2013.01); *A61F 2220/0008* (2013.01); *A61F 2230/005* (2013.01); *A61F 2230/0069* (2013.01); *A61F 2250/006* (2013.01); *A61F 2250/0039* (2013.01)

(56) References Cited

U.S. PATENT DOCUMENTS

| | | | |
|---|---|---|---|
| 3,997,923 A | 12/1976 | Possis | |
| 4,056,854 A | 11/1977 | Boretos et al. | |
| RE31,040 E | 9/1982 | Possis | |
| 4,506,394 A | 3/1985 | Bedard | |
| 4,705,516 A | 11/1987 | Barone et al. | |
| 4,790,843 A | 12/1988 | Carpentier et al. | |
| 4,994,077 A | 2/1991 | Dobben | |
| 5,032,128 A | 7/1991 | Alonso | |
| 5,332,402 A | 7/1994 | Teitelbaum | |
| 5,370,685 A | 12/1994 | Stevens et al. | |
| 5,397,351 A | 3/1995 | Pavcnik et al. | |
| 5,554,185 A | 9/1996 | Block et al. | |
| 5,716,370 A | 2/1998 | Williamson, IV et al. | |
| 5,855,601 A | 1/1999 | Bessler et al. | |
| 5,984,959 A | 11/1999 | Robertson et al. | |
| 6,074,418 A | 6/2000 | Buchanan et al. | |
| 6,106,550 A | 8/2000 | Magovern | |
| 6,129,756 A | 10/2000 | Kugler | |
| 6,168,614 B1 | 1/2001 | Andersen et al. | |
| 6,176,877 B1 | 1/2001 | Buchanan et al. | |
| 6,217,611 B1 | 4/2001 | Klostermeyer | |
| 6,419,696 B1 | 7/2002 | Ortiz et al. | |
| 6,425,916 B1 | 7/2002 | Garrison et al. | |
| 6,468,305 B1 | 10/2002 | Otte | |
| 6,569,196 B1 | 5/2003 | Vesely | |
| 6,645,242 B1 | 11/2003 | Quinn | |
| 6,730,121 B2 | 5/2004 | Ortiz et al. | |
| 6,764,508 B1 | 7/2004 | Roehe et al. | |
| 6,786,925 B1 | 9/2004 | Schoon et al. | |
| 6,790,229 B1 | 9/2004 | Berreklouw | |
| 6,846,325 B2 | 1/2005 | Liddicoat | |
| 6,893,459 B1 | 5/2005 | Macoviak | |
| 6,908,481 B2 | 6/2005 | Cribier | |
| 6,939,365 B1 | 9/2005 | Fogarty et al. | |
| 6,964,684 B2 | 11/2005 | Ortiz et al. | |
| 7,097,659 B2 | 8/2006 | Woolfson et al. | |
| 7,147,663 B1 | 12/2006 | Berg et al. | |
| 7,172,625 B2 | 2/2007 | Shu et al. | |
| 7,186,265 B2 | 3/2007 | Sharkawy et al. | |
| 7,291,168 B2 | 11/2007 | Macoviak et al. | |
| 7,300,463 B2 | 11/2007 | Liddicoat | |
| 7,311,730 B2 | 12/2007 | Gabbay | |
| 7,381,220 B2 | 6/2008 | Macoviak et al. | |
| 7,503,930 B2 | 3/2009 | Sharkawy et al. | |
| 7,513,909 B2 | 4/2009 | Lane et al. | |
| 7,527,646 B2 | 5/2009 | Rahdert et al. | |
| 7,578,843 B2 | 8/2009 | Shu | |
| 7,597,711 B2 | 10/2009 | Drews et al. | |
| 7,611,535 B2 | 11/2009 | Woolfson et al. | |
| 7,648,528 B2 | 1/2010 | Styre | |
| 7,691,144 B2 | 4/2010 | Chang et al. | |
| 7,708,775 B2 | 5/2010 | Rowe et al. | |
| 7,717,955 B2 | 5/2010 | Lane et al. | |
| 7,722,667 B1 | 5/2010 | Buchanan | |
| 7,758,640 B2 | 7/2010 | Vesely | |
| 7,771,469 B2 | 8/2010 | Liddicoat | |
| 7,871,436 B2 | 1/2011 | Ryan et al. | |
| 7,887,583 B2 | 2/2011 | Macoviak | |
| 7,951,197 B2 | 5/2011 | Lane et al. | |
| 7,959,674 B2 | 6/2011 | Shu et al. | |
| 7,981,153 B2 | 7/2011 | Fogarty et al. | |
| 8,025,695 B2 | 9/2011 | Fogarty et al. | |
| 8,083,793 B2 | 12/2011 | Lane et al. | |
| 8,105,377 B2 | 1/2012 | Liddicoat | |
| 8,163,013 B2 | 4/2012 | Machold et al. | |
| 8,187,207 B2 | 5/2012 | Machold et al. | |
| 8,287,591 B2 | 10/2012 | Keidar et al. | |
| 9,393,140 B2 | 7/2016 | Argentine et al. | |
| 2004/0034411 A1 | 2/2004 | Quijano et al. | |
| 2005/0137686 A1 | 6/2005 | Salahieh et al. | |
| 2006/0287717 A1 | 12/2006 | Rowe et al. | |
| 2008/0082166 A1 | 4/2008 | Styrc et al. | |
| 2008/0208327 A1 | 8/2008 | Rowe | |
| 2008/0275540 A1* | 11/2008 | Wen | A61F 2/2418 623/1.26 |
| 2008/0275548 A1 | 11/2008 | Svensson | |
| 2009/0240320 A1 | 9/2009 | Tuval et al. | |
| 2009/0287145 A1 | 11/2009 | Cragg et al. | |
| 2010/0076548 A1 | 3/2010 | Konno | |
| 2010/0161036 A1 | 6/2010 | Pintor et al. | |
| 2010/0179649 A1 | 7/2010 | Richter et al. | |
| 2010/0249915 A1 | 9/2010 | Zhang | |
| 2010/0312333 A1 | 12/2010 | Navia et al. | |
| 2011/0118822 A1 | 5/2011 | Welch | |
| 2011/0172765 A1 | 7/2011 | Nguyen et al. | |
| 2013/0144373 A1 | 3/2013 | Shahriari | |
| 2013/0103134 A1 | 4/2013 | Minion | |
| 2014/0316513 A1 | 10/2014 | Tang | |
| 2014/0330367 A1 | 11/2014 | Thapliyal | |
| 2015/0105850 A1 | 4/2015 | Shahriari | |
| 2015/0257881 A1 | 9/2015 | Bortlein | |
| 2016/0081787 A1 | 3/2016 | Parodi | |
| 2016/0081829 A1 | 3/2016 | Rowe | |

FOREIGN PATENT DOCUMENTS

| | | |
|---|---|---|
| EP | 2522306 | 11/2012 |
| FR | 2906454 | 4/2008 |
| WO | WO2000/047139 | 8/2000 |
| WO | WO2007/002423 | 1/2007 |
| WO | WO2007/081820 | 7/2007 |
| WO | WO2007/130537 | 11/2007 |
| WO | WO2007/149933 | 12/2007 |
| WO | WO2008/101193 | 8/2008 |
| WO | WO2014/197743 | 12/2014 |

OTHER PUBLICATIONS

Bonhoeffer P., et al., "Percutaneous Insertion of the Pulmonary Valve", Pediatric Cardiology, 2002; 39:1664-1669.
Anderson H R, et al., "Transluminal Implantation of Artificial Heart Valves", EUR Heart J., 1992; 13:704-708.
Anderson, H. R., et al., "Transluminal Catheter Implantation of New Expandable Artificial Cardiac Valve (the stent-valve) in the Aorta and the Beating Heart of Closed Chest Pigs", EUR Heart J.[Abstract], 1990;11 (Suppl):224a.
Hilbert S. L., "Evaluation of Explanted Polyurethane Tri Leaflet Cardiac Valve Prosthesis", J Thorac Cardiovascular Surgery, 1989; 94:419-29.
Block P C, "Clinical and Hemodynamic Follow-Up After Percutaneous Aortic Valvuloplasty in the Elderly", The American Journal of Cardiology, vol. 62, Oct. 1, 1998.
Boudjemline, Y., "Steps Toward Percutaneous Aortic Valve Replacement", Circulation, 2002; 105:775-558.
Bonhoeffer, P., "Transcatheter Implantation of a Bovine Valve in Pulmonary Position, a Lamb Study", Circulation, 2000: 102:813-816.
Boudjemline, Y., "Percutaneous Implantation of a Valve in the Descending Aorta in Lambs", EUR Heart J, 2002; 23:1045-1049.

(56) References Cited

OTHER PUBLICATIONS

Kulkinski, D., "Future Horizons in Surgical Aortic Valve Replacement: Lessons Learned During the Early Stages of Developing a Transluminal Implantation Technique", ASAIO J, 2004; 50:364-68.
PCT/US2016/049503, Communication Relating to the Results of the Partial International Search, dated Oct. 21, 2015.
PCT/US2016/049503, The International Search Report and the Written Opinion of the International Searching Authority, dated Jan. 13, 2017.
Chinese Office Action, CN Appln No. 201680049998.1, 11 pages dated Jul. 13, 2020.

* cited by examiner

STENT ASSEMBLIES INCLUDING PASSAGES TO PROVIDE BLOOD FLOW TO CORONARY ARTERIES AND METHODS OF DELIVERING AND DEPLOYING SUCH STENT ASSEMBLIES

CROSS-REFERENCE TO RELATED APPLICATIONS

This application is a divisional of U.S. patent application Ser. No. 14/841,749, filed Sep. 1, 2015, the contents of which are incorporated by reference herein in their entirety.

FIELD OF THE INVENTION

Embodiments hereof relate to heart valve prostheses and methods for intraluminally deploying heart valve prostheses, and in particular, to heart valve prostheses including coronary access and methods of intraluminally delivering and deploying such heart valve prostheses.

BACKGROUND OF THE INVENTION

Heart valves, such as the mitral, tricuspid, aortic, and pulmonary valves, are sometimes damaged by disease or by aging, resulting in problems with the proper functioning of the valve. Heart valve problems generally take one of two forms: stenosis in which a valve does not open completely or the opening is too small, resulting in restricted blood flow; or insufficiency in which blood leaks backward across a valve when it should be closed.

Heart valve replacement has become a routine surgical procedure for patients suffering from valve regurgitation or stenotic calcification of the leaflets. Conventionally, the vast majority of valve replacements entail full sternotomy in placing the patient on cardiopulmonary bypass. Traditional open surgery inflicts significant patient trauma and discomfort, requires extensive recuperation times, and may result in life-threatening complications.

To address these concerns, efforts have been made to perform cardiac valve replacements using minimally invasive techniques. In these methods, laparoscopic instruments are employed to make small openings through the patient's ribs to provide access to the heart. While considerable effort has been devoted to such techniques, widespread acceptance has been limited by the clinician's ability to access only certain regions of the heart using laparoscopic instruments.

Still other efforts have been focused upon percutaneous transcatheter (or transluminal) delivery of replacement cardiac valves to solve the problems presented by traditional open surgery and minimally invasive surgical methods. In such methods, a valve prosthesis is compacted for delivery in a catheter and then advanced, for example through an opening in the femoral artery and through the descending aorta to the heart, where the prosthesis is then deployed in the valve annulus (e.g., the aortic valve annulus).

Various types and configurations of prosthetic heart valves are used in percutaneous valve procedures to replace diseased natural human heart valves. The actual shape and configuration of any particular prosthetic heart valve is dependent to some extent upon the valve being replaced (i.e., mitral valve, tricuspid valve, aortic valve, or pulmonary valve). In general, prosthetic heart valve designs attempt to replicate the function of the valve being replaced and thus will include valve leaflet-like structures used with either bioprostheses or mechanical heart valve prostheses. If bioprostheses are selected, the replacement valves may include a valved vein segment or pericardial manufactured tissue valve that is mounted in some manner within an expandable stent frame to make a valved stent. In order to prepare such a valve for percutaneous implantation, one type of valved stent can be initially provided in an expanded or uncrimped condition, then crimped or compressed around a balloon portion of a catheter until it is close to the diameter of the catheter. In other percutaneous implantation systems, the stent frame of the valved stent can be made of a self-expanding material. With these systems, the valved stent is crimped down to a desired size and held in that compressed state within a sheath, for example. Retracting the sheath from this valved stent allows the stent to expand to a larger diameter, such as when the valved stent is in a desired position within a patient.

While some problems of traditional open-heart surgery are overcome by percutaneous transcatheter (transluminal) methods, there are still risks associated with the method including post implantation percutaneous coronary intervention, coronary perfusion, and heart block.

Post implantation coronary access with traditional transcatheter valve implantation (TAVI) may be limited by factors such as implantation height, strut width and cell opening size. Despite technical efforts to optimize valve prostheses placement, these factors may limit future access to coronary arteries and procedures to coronary arteries following transcatheter valve implementation.

Coronary perfusion refers to the pressure gradient between aortic pressure and left ventricle pressure. This gradient drives blood flow into the coronary arteries. Implantation placement, height, cell opening size, partial coronary obstruction, and stent alignment may negatively impact blood flow to the coronary arteries.

Heart block is an abnormal heart rhythm where the heart beats too slowly, called bradycardia. With heart block, the electrical signals that provide normal heart rhythm are either partially or totally blocked between the upper and lower heart. Improper placement of an aortic valve prosthesis is considered a possible contributor to heart block.

There is a need for devices and methods that allow for simultaneous creation of coronary access during transcatheter valve implementation (TAVI) procedures. There is also a need for devices and methods to deploy valve prostheses further from the aortic annulus to minimize heart block in patients undergoing transcatheter valve implantation (TAVI) procedures.

BRIEF SUMMARY OF THE INVENTION

Embodiments hereof are related to an anchor stent assembly to be used with a valve component. The anchor stent assembly has a radially compressed delivery configuration and a radially expanded deployed configuration. The stent assembly includes a generally tubular frame having a first end and a second end, the frame defining a central passage and a central axis. A secondary passage is defined between an inner surface of the frame and an outer surface of an inner rib disposed closer to the central axis than the frame. An extension tube is disposed through the secondary passage. The extension tube includes an extension tube lumen having a first opening at a first end of the extension tube and a second opening at a second end of the extension tube. The anchor stent assembly may include two secondary passages with two extension tubes such that the anchor stent assembly may be deployed in the aorta and the extension tubes may be circumferentially aligned with respective ostia of the left and right coronary arteries.

Embodiments hereof are also directed to a method of implanting a stent assembly at a location in an aorta. The method includes advancing the stent assembly in a radially compressed delivery configuration to the location in the aorta. The stent assembly includes a generally tubular frame having a first end and a second end, a central passage, a central axis, a secondary passage formed between an inner surface of the frame and an outer surface of an inner rib closer to the central axis than the frame, and an extension tube extending through the secondary passage, the extension tube being coupled to the frame and having an extension tube lumen. The method further includes rotationally orienting the stent assembly such that the extension tube is generally circumferentially aligned with an ostium of a coronary artery. The stent assembly is then deployed from the radially compressed delivery configuration to a radially expanded deployed configuration at the location within the aorta. With the stent assembly in place, a coronary stent is advanced in a radially compressed delivery configuration through the extension tube lumen such that a first portion of the coronary stent resides within the extension tube lumen and a second portion of the coronary stent extends into the coronary artery. The coronary stent is then deploying the coronary stent assembly from the radially compressed delivery configuration to a radially expanded deployed configuration. The method may further include delivering a valve component in a radially compressed delivery configuration to a location within a native aortic valve and deploying the valve component such that the valve component expands from the radially compressed delivery configuration to a radially expanded configuration. The valve component may be situated such that a portion of the valve component is disposed within the central passage of the anchor stent assembly when both are deployed.

Embodiments hereof are also directed to an anchor stent assembly for use with a valve component. The anchor stent assembly includes a radially compressed delivery configuration and a radially expanded deployed configuration. The stent assembly includes a generally tubular frame having a proximal end and a distal end and defining a central passage and a central axis. A secondary passage is defined between an inner surface of the frame and an outer surface of an inner rib closer to the central axis than the frame. A proximal alignment arm is coupled to the frame at the proximal end of the frame. A skirt is coupled to the inner rib and the proximal alignment arm such that a coronary channel is defined between an outer surface of the skirt and the frame. In an embodiment, the secondary passage comprises two secondary passages, and the stent assembly is configured to be rotationally oriented such that one of the secondary passages is circumferentially aligned with an ostium of the left coronary artery and the other of the secondary passages is circumferentially aligned with an ostium of the right coronary artery. The portion of the skirt attached to the proximal alignment arm defines a coronary pocket between the outer surface of the skirt and the aortic sinus in which the proximal alignment arm is disposed.

Embodiments hereof are also directed to a method of implanting an anchor stent assembly at a location within an aorta. The anchor stent assembly includes a frame with a central passage and a central axis, a secondary passage formed between an inner surface of the frame and an outer surface of an inner rib closer to the central passage, a proximal alignment arm extending proximally from a proximal end of the frame, and a skirt coupled to the inner rib and the proximal alignment arm. The anchor stent assembly is advanced in a radially compressed delivery configuration to the location in the aorta. The method includes rotationally orienting the anchor stent assembly such that the secondary passage is generally circumferentially aligned with an ostium of a coronary artery. The method further includes deploying the anchor stent assembly from the radially compressed delivery configuration to a radially expanded deployed configuration at the location within the aorta such that the proximal alignment arm extends into an aortic sinus below the ostium of the coronary artery and a coronary channel is formed between an outer surface of the skirt at the inner rib and an inner surface of aorta, and a coronary pocket is formed between the outer surface of the skirt at the proximal alignment arm and an inner surface of the aortic sinus. The method may further include delivering a valve component in a radially compressed delivery configuration to a location within a native aortic valve, and deploying the valve component such that the valve component expands from the radially compressed delivery configuration to a radially expanded deployed configuration.

Embodiments hereof are also directed to a valve assembly including a generally tubular frame, a prosthetic valve coupled to the frame, a coronary orifice extending between an inner surface and an outer surface of the frame, and a coronary arm having a first end coupled to the coronary orifice. The coronary arm has a generally tubular structure and defines a longitudinal passage with a longitudinal axis. The coronary arm includes a longitudinally collapsed delivery configuration wherein a second end of the coronary arm is adjacent the first end, and a longitudinally extended deployed configuration wherein the second end is spaced from the first end. The prosthetic valve may include two coronary arms and is configured to be deployed at a native aortic valve such that one of the coronary arms extends into the left coronary artery and the other coronary arm extends into the right coronary artery.

Embodiments hereof are also directed to a method of implanting a valve assembly at a location of a native valve. The valve assembly includes a generally tubular frame defining a central passage and a central axis. A prosthetic valve is coupled to the frame. A coronary orifice extends between an inner surface and an outer surface of the frame. A coronary arm includes a first end coupled to the coronary orifice of the frame. A second end of the coronary arm is disposed adjacent to the first end with the coronary arm in a longitudinally collapsed delivery configuration. The method includes advancing the valve assembly in a radially compressed delivery configuration with the coronary arm in the longitudinally collapsed configuration to the location of the native valve. The valve assembly is rotationally oriented such that the coronary arm is aligned with an ostium of a coronary artery. The valve assembly is deployed such that the frame expands from the radially compressed delivery configuration to a radially expanded deployed configuration with the frame engaging an inner surface of the native valve and the aortic sinuses. The coronary arm is from the longitudinally compressed delivery configuration to a longitudinally extended deployed configuration such that the second end of the coronary arm is extended away from the first end and the second end is disposed within the coronary artery. The valve assembly may include two coronary arms, and the method includes rotationally orienting the valve assembly such that one of the two coronary arms is aligned with the left coronary artery and the other of the two coronary arms is aligned with the right coronary artery.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" when used in the following description to refer to a catheter or delivery system are with respect to a position or direction relative to the treating clinician. Thus, "distal" and "distally" refer to positions distant from or in a direction away from the clinician and "proximal" and "proximally" refer to positions near or in a direction toward the clinician. When the terms "distal" and "proximal" are used in the following description to refer to a device to be implanted into a vessel, such as an anchor stent assembly or valve component, they are used with reference to the direction of blood flow from the heart. Thus, "distal" and "distally" refer to positions in a downstream direction with respect to the direction of blood flow and "proximal" and "proximally" refer to positions in an upstream direction with respect to the direction of blood flow.

Figure 1:
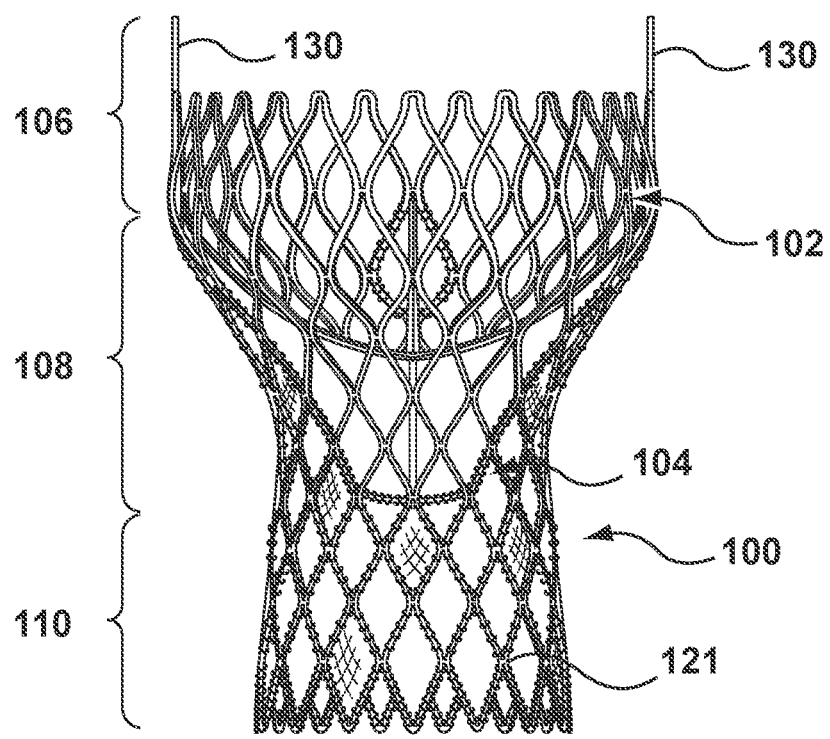
FIG. 1 is a schematic illustration of a prior art stented valve prosthesis.
Figure 2:
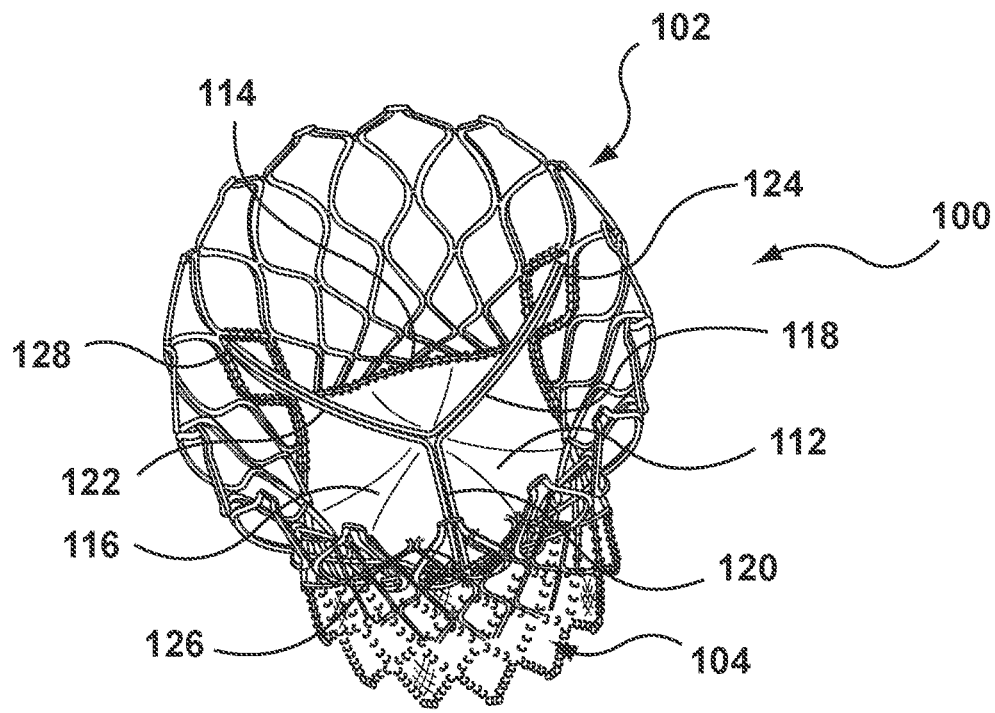
FIG. 2 is a schematic illustration of the prior art stented valve prosthesis of FIG. 1.

FIGS. 1 and 2 show an exemplary conventional valve prosthesis similar to the Medtronic CoreValve® transcatheter aortic valve replacement valve prosthesis and as described in U.S. Patent Application Publication No. 2011/0172765 to Nguyen et al. (hereinafter "the '765 publication"), which is incorporated by reference herein in its entirety. As shown in FIGS. 1 and 2, valve prosthesis 100 includes an expandable generally tubular frame 102 having a valve body 104 affixed to its interior surface, e.g., by sutures. Frame 102 preferably comprises a self-expanding structure formed by laser cutting or etching a metal alloy tube comprising, for example, stainless steel or a shape memory material such as nickel titanium. The frame has an expanded deployed configuration, which is impressed upon the metal alloy tube using techniques known in the art. Valve body 104 preferably comprises individual leaflets assembled to a skirt, where all of the components are formed from a natural or man-made material, including but not limited to, mammalian tissue, such as porcine, equine or bovine pericardium, or a synthetic or polymeric material.

Frame 102 in the exemplary embodiment includes an outflow section 106, an inflow section 110, and a constriction region 108 between the inflow and outflow sections. Frame 102 may comprise a plurality of cells having sizes that vary along the length of the prosthesis. When configured as a replacement for an aortic valve, inflow section 110 extends into and anchors within the aortic annulus of a patient's left ventricle and outflow section 106 is positioned in the patient's ascending aorta. Frame 102 also may include eyelets 130 for use in loading the heart valve prosthesis 100 into a delivery catheter.

Valve body 104 may include a skirt 121 affixed to frame 102, and leaflets 112, 114, 116. Leaflets 112, 114, 116 may be attached along their bases to skirt 121, for example, using sutures or a suitable biocompatible adhesive. Adjoining pairs of leaflets are attached to one another at their lateral ends to form commissures 124, 126, 128, with free edges 118, 120, 122 of the leaflets forming coaptation edges that meet in an area of coaptation, as described in the '765 publication and shown in FIG. 2 hereof.

The following detailed description is merely exemplary in nature and is not intended to limit the invention or the application and uses of the invention. Although the description of the invention is in the context of transcatheter aortic valve implantation, the invention may also be used in any other body passageways where it is deemed useful. Furthermore, there is no intention to be bound by any expressed or implied theory presented in the preceding technical field, background, brief summary or the following detailed description.

Figure 3:
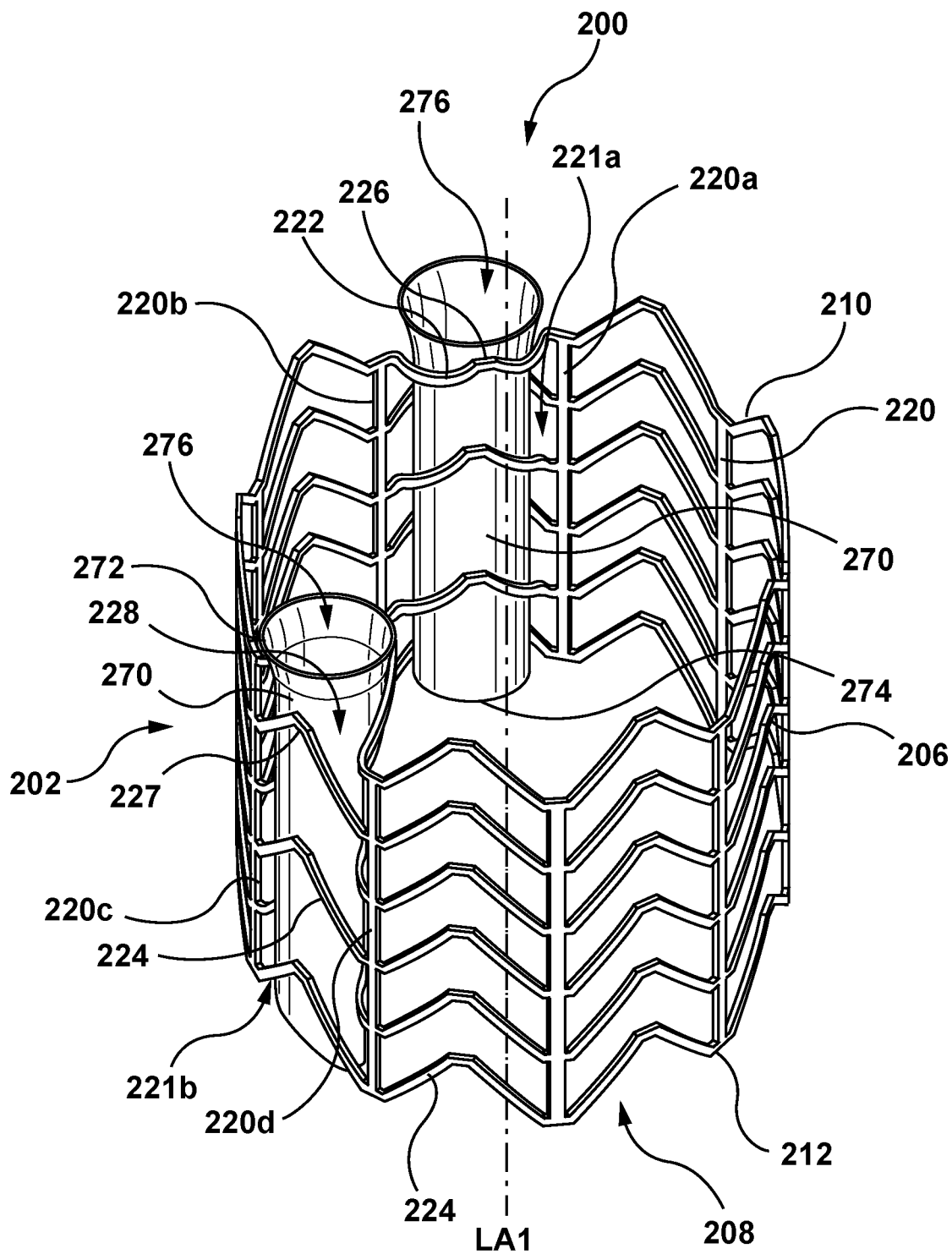
FIG. 3 is a schematic illustration of an anchor stent assembly in accordance with an embodiment hereof.

FIG. 3 shows an embodiment of an anchor stent assembly 200 including an anchor stent 202 and extension tubes 270. Anchor stent 202 is sized and designed to deploy in the aorta above the aortic sinuses of a heart, as described in more detail below. Anchor stent assembly is configured to be used with a valve component, as will be described in more detail below.

Anchor stent 202 includes a frame 206 having a first or proximal end 212, and a second or distal end 210, as shown in FIG. 3. Frame 206 is a generally tubular configuration having a central passage 208. Frame 206 is a stent structure as is known in the art and may be self-expanding. Frame 206 includes a first, radially compressed configuration for delivery and a second, radially expanded or deployed configuration when deployed at the desired site. In the radially expanded configuration, frame 206 may have a diameter that is generally about 2-5 millimeters larger than the diameter of the location in which the frame is to be installed, in order to create opposing radial forces between the outward radial force of the frame against an inward resisting force of the vessel.

Frame 206 is constructed of a series of vertical struts or stringers 220 arranged parallel to a central longitudinal axis LA1 of frame 206. Stringers 220 are spaced radially from the central longitudinal axis LA1 and are spaced circumferentially from each other around a circumference of the frame 206. Stringers 220 are connected by a series of radially collapsible outer struts or ribs 224 that run circumferentially between adjacent stringers 220. The outer surfaces of outer ribs 224 and the outer surfaces of stringer 220 form the outer surface of frame 206. While the embodiment of FIG. 3 shows anchor stent 206 with ten (10) stringers 220 connected by six (6) rows of outer ribs 224, it is not meant to limit the design, and it is understood that more or fewer stringers 220 and outer ribs 224 may be provided depending on the specific requirements of the components, devices, and procedures being utilized.

A first extension tube channel or secondary passage 221a is formed between adjacent stringers 220a and 220b and between outer ribs 224 and corresponding inner ribs 222 disposed between stringers 220a and 220b. Inner ribs 222 are disposed closer to central longitudinal axis LA1 than outer ribs 224 such that first extension tube channel 221a is formed between outer ribs 224 and inner ribs 222 and first extension tube channel 221a extends longitudinally from first end 212 to second end 210 of frame 206. Similarly, a second extension tube channel or secondary passage 221b is formed between adjacent stringers 220c and 220d and between outer ribs 224 and corresponding inner ribs 222 disposed between stringers 220c and 220d. Inner ribs 222 are disposed closer to central longitudinal axis LA1 than outer ribs 224 such that second extension tube channel 221b is formed between outer ribs 224 and inner ribs 222 and second extension tube channel 221b extends from first end 212 to second end 210 of frame 206. First and second extension tube channels 221a/221b are spaced apart from each other around the circumference of frame 206 such that they generally align with circumferentially with a corresponding coronary artery when deployed adjacent the aortic sinuses of an aortic valve. Thus, first and second extension tube channels 221a/221b are generally spaced circumferentially approximately 120 degrees apart.

Stringers 220, outer ribs 224 and inner ribs 222 are collapsible structures and may be constructed of materials such as, but not limited to, stainless steel, Nitinol, or other suitable materials for the purposes disclosed herein. Outer ribs 224 and inner ribs 222 may be connected to stringers 220 by methods such as, but not limited to fusing, welding, or other methods suitable for the purposes disclosed herein. Alternatively, frame 206, including stringers 220, outer ribs 224, and inner ribs 222 may be formed by cutting a pattern from a tube, such as by laser-cutting, chemical etching, or other suitable methods. In other embodiments, the pattern may be cut from a flat sheet of material and then rolled to form frame 206. Although frame 206 has been described with stringers 220, outer ribs 224, and inner ribs 222, other structures may be used to form frame 206, such as, but not limited to, rings formed from sinusoidally shaped struts, struts forming cells (such as diamond shaped or hexagonally shaped cells), and other structures. The details of such structures are not essential provided that the frame includes a central passage and at least one secondary passage as described herein.

Extension tubes 270 are disposed within respective extension tube channels 221a/221b of frame 206. In the embodiment shown, extension tubes 270 extend from first end 212 to second end 210 of frame 206. However, in other embodiments, extension tubes need not extend the entire length of frame 206. Extension tubes 270 include a first end 272 adjacent first end 212 of frame 206, and a second end 274 adjacent second end 210 of anchor frame 206. First end 272 of extension tube 270 may be flared as shown such that the diameter of first end 272 is greater than the diameter of second end 274. Each extension tube 270 forms a respective extension tube lumen 276. Extension tube 270 is constructed of materials such as, but not limited to woven polyester, Dacron mesh, and PTFE (woven, mesh, or elecrospun), or other materials suitable for the purposes disclosed herein. Extension tube 270 may be connected to anchor frame 206 at inner rib contact point 226 and outer rib contact point 227 and may be attached by methods such as, but not limited to sutures, adhesives, fusing, welding, or other methods suitable for the purposes disclosed herein.

Although the embodiment of FIG. 3 has been shown with extension tube channels 220a/220b with a respective extension tube 270 disposed therein, both the extension tube channels 220 and extension tubes 270 are not required. For example, and not by way of limitation, in another embodiment, extension tube channels 220 are eliminated and extension tubes are attached to an inner surface of outer ribs 224, In such an embodiment, inner ribs 222 are eliminated such that extension tube channels 220 are not formed. In another example, extension tube channels 220 are formed, but extension tubes 270 are not disposed therein. Instead, respective coronary stents, as described in more detail below, may extend through extension tube channels 220. In such an embodiment, it is preferable that the coronary stents are covered stents or stent grafts.

Figure 4A:
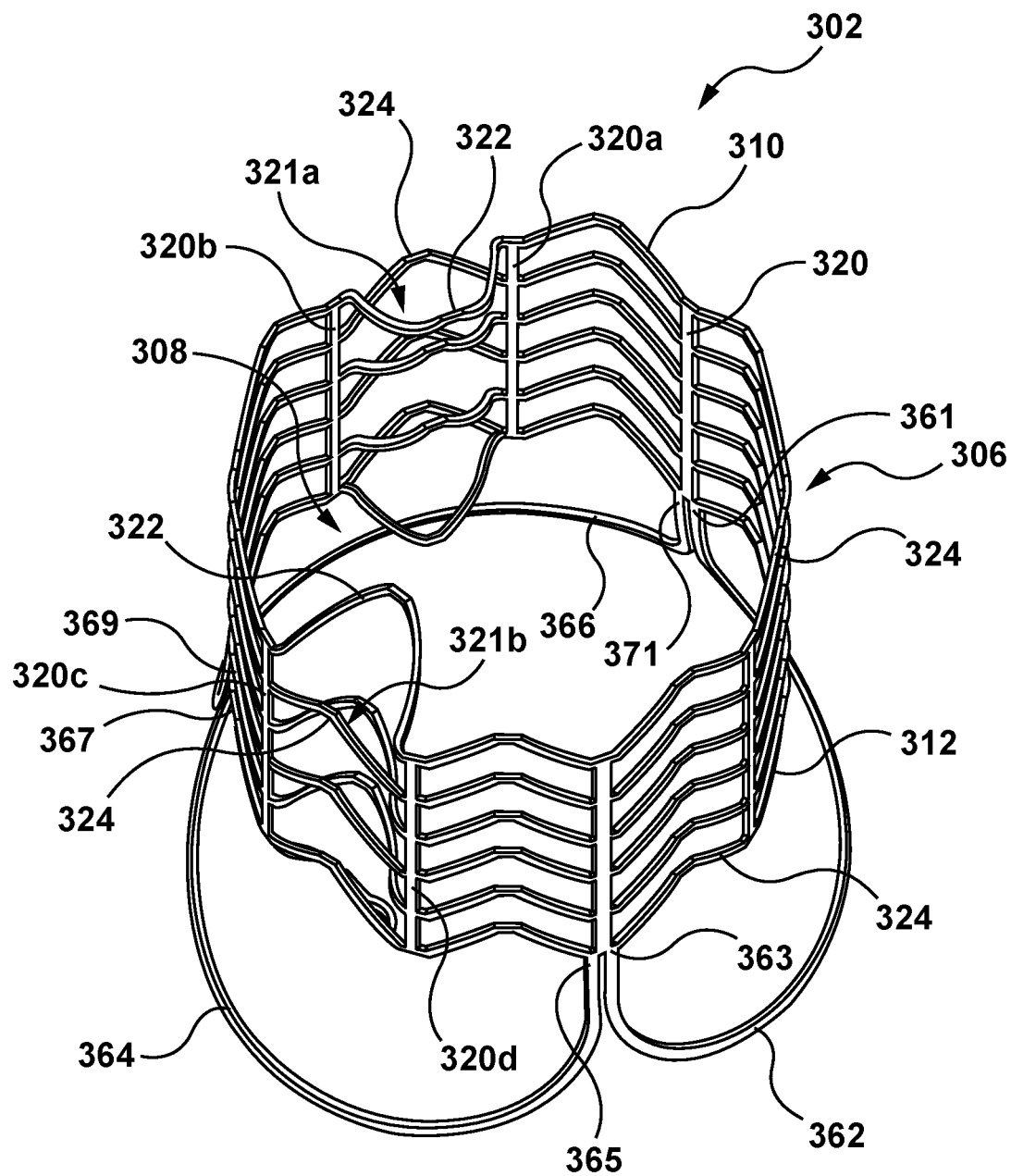
FIGS. 4A and 4B are schematic illustrations of an anchor stent assembly in accordance with another embodiment hereof.
Figure 4B:
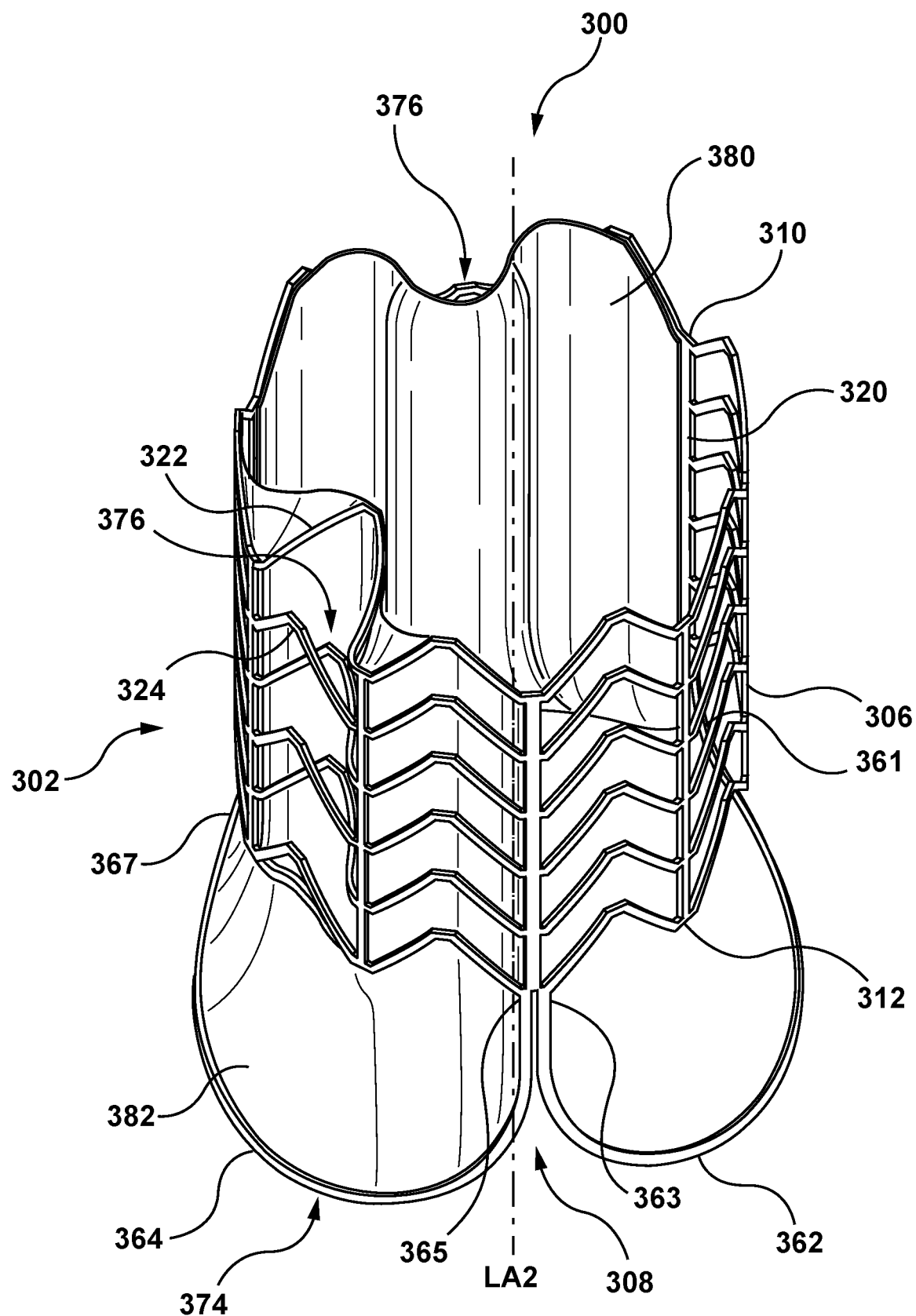

Another embodiment of an anchor stent assembly 300 is shown in FIGS. 4A and 4B. Anchor stent assembly 300 includes an anchor stent 302 including proximal alignment arms and a skirt to form coronary pockets, as described in more detail below. Anchor stent 302 is sized and configured to be deployed within the aorta, above the aortic sinuses of a heart, with the proximal alignment arms extending into aortic sinuses, as described in more detail below.

Anchor stent 302 includes a frame 306 having a first or proximal end 312, and a second or distal end 310, as shown in FIGS. 4A and 4B. Frame 306 is a generally tubular configuration having a central passage 308. Frame 306 is a stent structure as is known in the art and may be self-expanding. Frame 306 includes a first, radially compressed configuration for delivery and a second, radially expanded or deployed configuration when deployed at the desired site. Frame 306 may be constructed of materials such as, but not limited to, stainless steel, Nitinol, or other suitable materials for the purposes disclosed herein. In the radially expanded configuration, frame 306 may have a diameter that is generally about 2-5 millimeters larger than the diameter of the location in which the frame is to be installed, in order to create opposing radial forces between the outward radial force of the frame against an inward resisting force of the vessel.

Frame 306 is constructed of a series of vertical struts or stringers 320 360 arranged parallel to a central longitudinal axis LA2 of frame 306. Stringers 320 are spaced radially from the central longitudinal axis LA2 and are spaced circumferentially from each other around the circumference of frame 306. Stringers 320 are connected by a series of radially collapsible outer struts or ribs 324 that run circumferentially between adjacent stringers 320. The outer surfaces of outer ribs 324 and the outer surfaces of stringers 320 for the outer surface of frame 306. While the embodiment of FIG. 4A shows anchor stent 302 with ten (10) stringers 320 connected by six (6) rows of outer ribs 324, it is not meant to limit the design, and it is understood that more or fewer stringers 320 and outer ribs 324 may be provided depending on the specific requirements of the components, devices, and procedures being utilized.

A first extension channel or secondary passage 321a is formed between adjacent stringers 320a and 320b and between outer ribs 324 and corresponding inner ribs 322 disposed between stringers 320a and 320b. Inner ribs 322 are disposed closer to central longitudinal axis LA2 than outer ribs 324 such that first extension channel 321a is formed between outer ribs 324 and inner ribs 322 and first extension channel 321a extends longitudinally from first end 310 to second end 312. Similarly, a second extension channel or secondary passage 321b is formed between adjacent stringers 320c and 320d and between outer ribs 324 and corresponding inner ribs 322 disposed between stringers 320c and 320d. Inner ribs 322 are disposed closer to central longitudinal axis LA1 than outer ribs 324 such that second extension channel 321b is formed between outer ribs 324 and inner ribs 322 and second extension channel 321b extends from first end 312 to second end 310 of frame 306. First and second extension channels 321a/321b are spaced apart from each other around the circumference of frame 306 such that they generally align circumferentially with a corresponding coronary artery when deployed adjacent the aortic sinuses of an aortic valve. Thus, first and second channels 321a/321b are generally spaced circumferentially approximately 120 degrees apart.

As described above, frame 306 is generally similar to frame 206 of FIG. 3. As explained with respect to frame 206, stringers 320, outer ribs 324 and inner ribs 322 of frame 306 are collapsible structures such as wire and may be constructed of materials such as, but not limited to, stainless steel, Nitinol, or other suitable materials for the purposes disclosed herein. Outer ribs 324 and inner ribs 322 may be connected to stringers 320 by methods such as, but not limited to fusing, welding, or other methods suitable for the purposes disclosed herein. Alternatively, frame 306, including stringers 320, outer ribs 324, and inner ribs 322 may be formed by cutting a pattern from a tube, such as by laser-cutting, chemical etching, or other suitable methods. In other embodiments, the pattern may be cut from a flat sheet of material and then rolled to form frame 306. Although frame 306 has been described with stringers 320, outer ribs 324, and inner ribs 322, other structures may be used to form frame 306, such as, but not limited to, rings formed from sinusoidally shaped struts, struts forming cells (such as diamond shaped or hexagonally shaped cells), and other structures. The details of such structures are not essential provided that the frame includes a central passage and at least one extension channel as described herein.

Anchor stent 302 further includes proximal alignment arms 362, 364, and 366 extending proximally from first end 312 of frame 306. In the embodiment shown in FIGS. 4A and 4B, each proximal alignment arm 362, 364, and 366 is in the form of a wire loop with first and second ends of the wire attached to frame 306. In particular, first arm 362 includes first and second ends attached to frame 306 at connections 361 and 363 respectively, as shown in FIG. 4A. Similarly, second arm 364 includes first and second ends attached to frame 306 at connections 365 and 367, respectively, and third arm 366 includes first and second ends attached to frame 306 at connections 369 and 371, respectively. Connections 361, 363, 365, 367, 369, and 371 may be formed by the material of proximal alignment arms 362, 364, and 366, and frame 306 being fused or welded together. Alternatively, the connections may be mechanical connections such as, but not limited to, sutures or otherwise tied, a crimp connector to crimp ends of the arms to frame 306, or other suitable connections. Proximal alignment arms 362, 364, and 366 include a radially compressed configuration for delivery to the treatment site and a radially expanded or deployed configuration. In the radially expanded configuration, proximal alignment arms 362, 364, and 366 have a combined diameter such that they fit into the aortic sinuses. For example, and not by way of limitation, in the radially expanded configuration, the combined diameter of proximal alignment arms 362, 364, and 366 may be in the range of 29 mm-39 mm. As shown in FIGS. 4A and 4B, in the radially expanded configuration, proximal alignment arms 362, 364, and 366 flare outwardly from first end 312 of frame 306. Although FIG. 4A shows three (3) proximal alignment arms with connections approximately equally spaced around the circumference of frame 306, more or fewer arms may be utilized, and the arms need not be equally spaced around the circumference of frame 306. At least two of the proximal alignment arms (364 and 366 in FIG. 4A) are configured such that they encircle, but do not obstruct, the left and right ostia of the coronary arteries, as described in more detail below.

Anchor stent assembly 300 further includes a skirt 380 attached to an inside surface thereof to separate central passage 308 from extension channels 321a and 321b, as shown in FIG. 4B. As shown in FIG. 4B, skirt 380 has a second end 372 coupled to second end 310 of anchor frame 306 and a first end 374 coupled to proximal alignment arms 362, 364, and 366. An outer surface of skirt 380 forms a coronary pocket 382 at each of proximal alignments arms 362, 364, 366. The coronary pocket 382 formed with skirt 380 and proximal alignment arm 364 is generally longitudinally aligned with extension channel 321b. The coronary pocket 382 formed with skirt 380 and proximal alignment arm 366 (not shown in FIG. 4B) is generally longitudinally aligned with extension channel 321a. Coronary pockets 382 encircle the left and right coronary ostia when anchor stent assembly 300 is in the radially expanded configuration at the desired deployment site, as shown in more detail below. Skirt 380 is a generally cylindrical tube constructed of cloth or fabric material. The fabric may comprise any suitable material including, but not limited to, woven polyester such as polyethylene terephthalate, polytetrafluoroethylene (PTFE), or other biocompatible materials. Skirt 380 is secured to frame 306 and the proximal alignment arms in a manner such as, but not limited to, sutures, laser or ultrasonic welding, or other methods suitable for the purposes disclosed herein. In another embodiment, first end 374 of skirt 380 may be coupled to first end 312 of frame 306 such that skirt 380 does not extend proximally to the proximal alignment arms. In such an embodiment, extension channels 321a, 321b are generally circumferentially aligned with the coronary ostia, but disposed above the ostia, and the proximal alignment arms 364, 366 encircle the ostia to assist in prevent blockage thereof by a valve component, described in more detail below.

With anchor stent assembly deployed with frame 306 in the aorta and proximal alignment arms 362, 364, 366 disposed within the aortic sinuses, skirt 380 is configured such that the wall of the aortic sinuses and skirt 380 attached to frame 306 and inner ribs 322 enclose extension channels 321 such that each extension channel 321 and corresponding coronary pocket 382 forms a coronary channel 376 for direct path for blood flow to the left or right coronary ostia.

An embodiment of a method of delivering and deploying an anchor stent assembly and a corresponding valve component is schematically represented in FIGS. 5-13. FIGS. 5-13 describe the method with respect to anchor stent assembly 200 of FIG. 3. FIGS. 5-13 are not drawn to scale regarding relative lengths of anchor stent assembly 200 and the valve component. The valve component is identified herein as valve component 240. Valve component 240 is generally includes a prosthetic valve 250 attached to a frame 242 (shown schematically in FIG. 13). The combination of frame 242 and prosthetic valve 250 can assume various configurations. For example, and not by way of limitation, valve component 240 may be similar to valve prosthesis 100 shown in FIGS. 1-2. Further, valve component 240 may be similar to the valve component described in U.S. Patent Application Publication No. 2015/0119974, including a common inventor herewith and assigned to Medtronic, Inc., the contents of which are incorporated by reference herein in their entirety.

Figure 5:
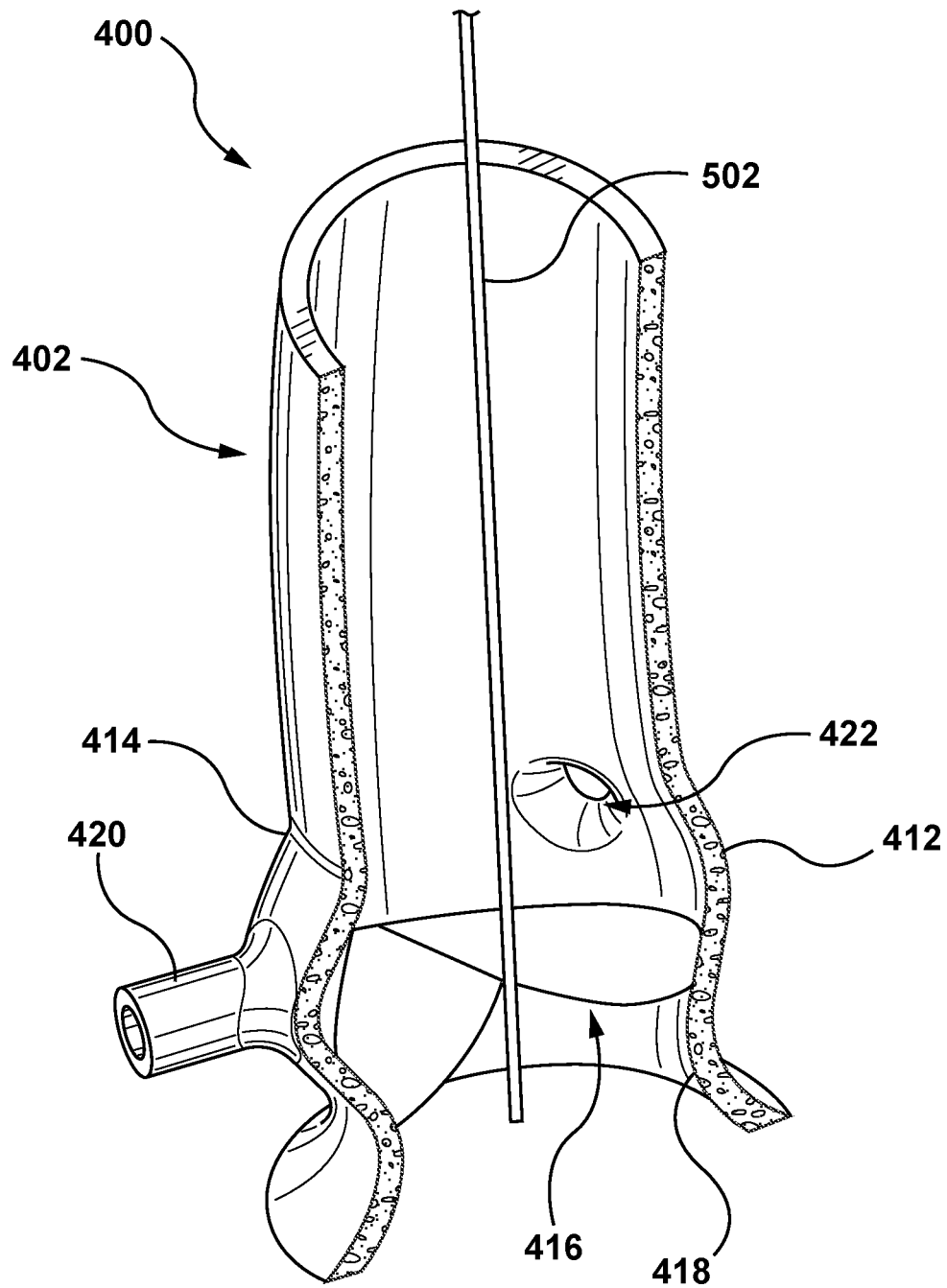
FIGS. 5-13 are schematic illustrations of an embodiment of a method for delivering and deploying a valve prosthesis at an aortic valve with the anchor stent assembly of FIG. 3 deployed in the aorta above the aortic sinuses.

In the method, a guidewire 502 is advanced distally, i.e., away from the clinician, through the aorta 400, past the sinotubular junction 414, and into the aortic sinuses 412 in the region of the aortic valve 416 and annulus 418, as shown in FIG. 5. Guidewire 502 may be introduced through an opening or arteriotomy through the wall of femoral artery in the groin region of the patient by methods known to those skilled in the art, such as, but not limited to, the Seldinger technique. Guidewire 502 is advanced into the descending (or abdominal) aorta (not shown), the aortic arch (not shown), and the ascending aorta 402, as shown in FIG. 5. FIG. 5 also shows two coronary arteries 420 and their corresponding coronary ostia 422. Although FIGS. 5-13 show a retrograde percutaneous femoral procedure, it is not meant to limit the method of use and other procedural methods may be used. For example, and not by way of limitation, retrograde percutaneous implantation via subclavian/axillary routes, direct apical puncture, and the use of direct aortic access via either ministernotomy or right anterior thoracotomy may also be used.

Figure 6:
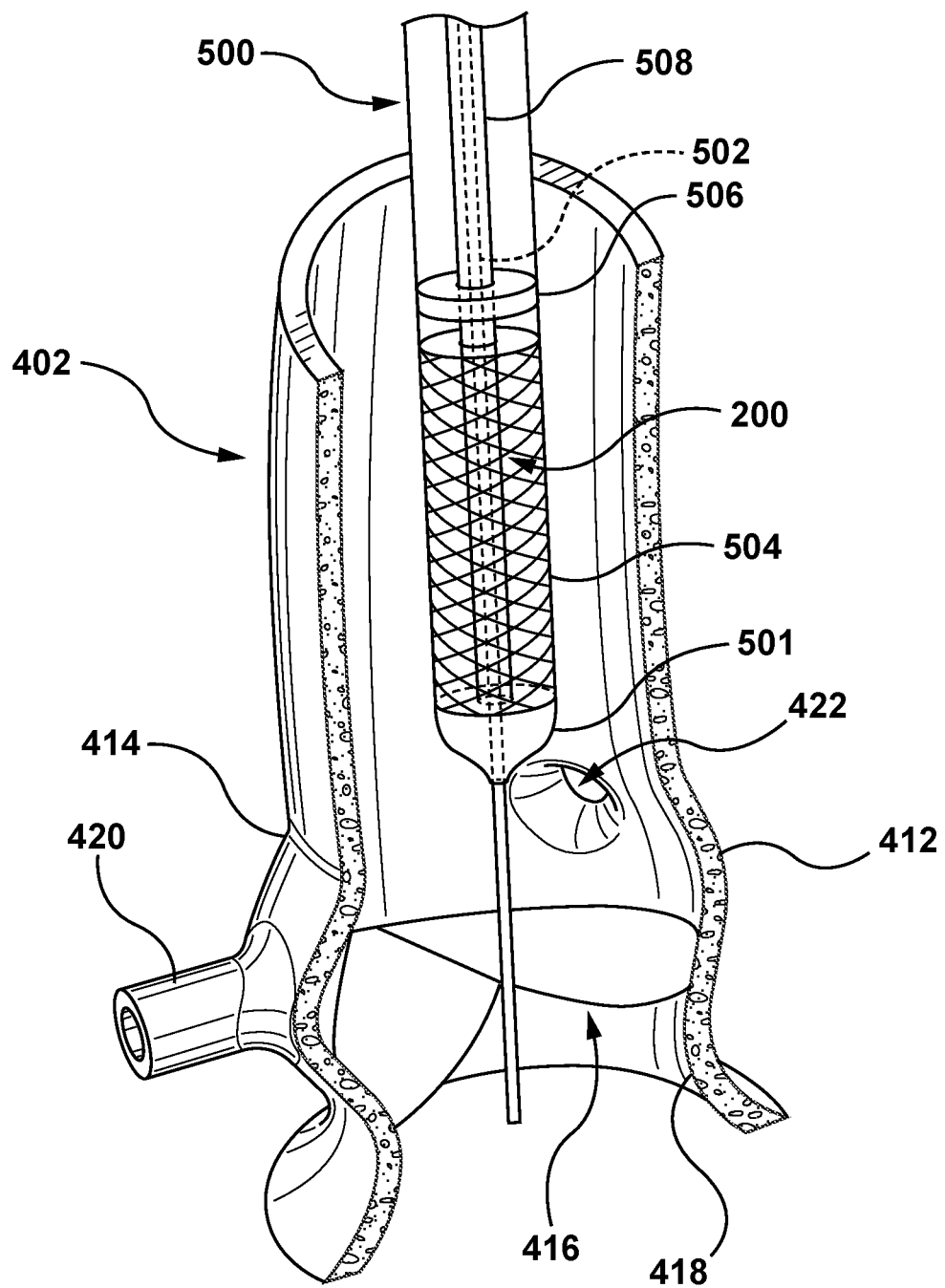

FIG. 6 shows a delivery system 500 for delivering anchor stent assembly 200 being advanced distally, i.e., away from the clinician, over guidewire 502 to a location in ascending aorta 402 adjacent the aortic sinuses 412. Delivery system 500 may be any suitable delivery system for delivering stents and/or stent grafts. In the embodiment shown schematically, anchor stent assembly 200 includes a self-expanding anchor stent 202 and extension tubes 270. Accordingly, delivery system 500 generally includes an inner or guidewire shaft 508, which includes a guidewire lumen (not shown) for receiving guidewire 502. A proximal end of guidewire 502 may be back loaded into the guidewire lumen (not shown) of inner shaft 508 through a distal opening (not shown) in inner shaft 508. Delivery system 500 may be an over-the-wire type catheter, or a rapid exchange catheter, or other catheter devices. Delivery system 500 further generally may include a distal tip 501, an outer sheath 504 that maintains anchor stent assembly 200 in the radially compressed or delivery configuration during intraluminal delivery through the vasculature, as shown in FIG. 6, and may also include a pusher or stopper 506, and other features. Delivery system 500 and/or anchor stent assembly 200 may also include, for example, radiopaque markers such that the clinician may determine when delivery system 500 and/or anchor stent assembly 200 is in the proper location and alignment for deployment.

Figure 7:
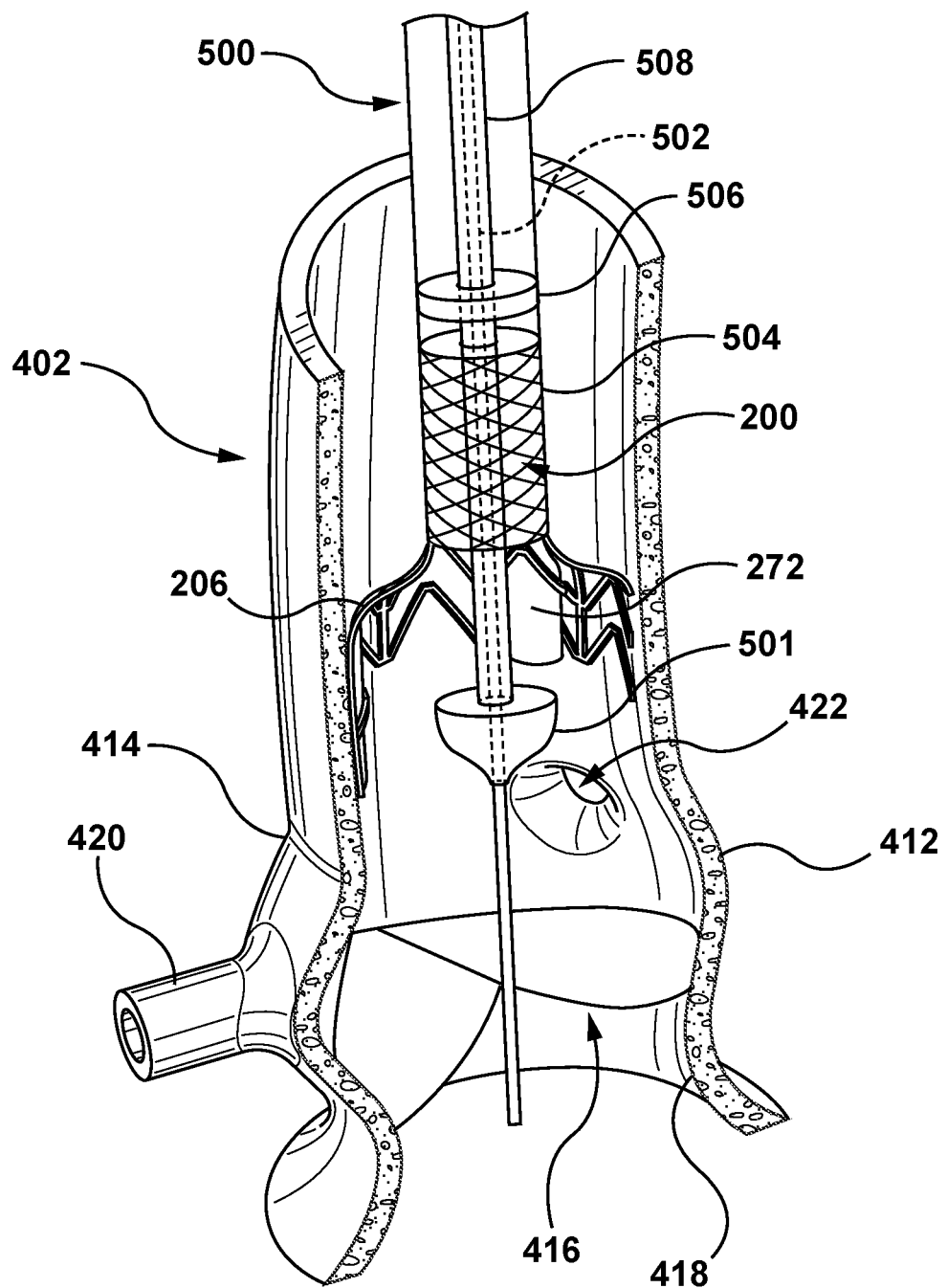

Once delivery system 500 has been advanced to the desired location, such as when first end 212 of anchor stent 202 is generally aligned with sinotubular junction 414, and extension tubes 270 rotationally aligned with coronary ostia 422, outer sheath 504 is retracted proximally, i.e., towards the clinician, as shown in FIG. 7. As outer sheath 504 is retracted, frame 206 of anchor stent 202 expands radially outward, engaging the inner wall of the ascending aorta 402, as shown in FIG. 7.

Outer sheath 504 is further retracted proximally, i.e., towards the clinician, to complete deployment of anchor stent assembly 200 from outer sheath 504. In other words, sheath 504 is retracted such that anchor stent assembly 200 is no longer constrained by sheath 504.

Figure 8:
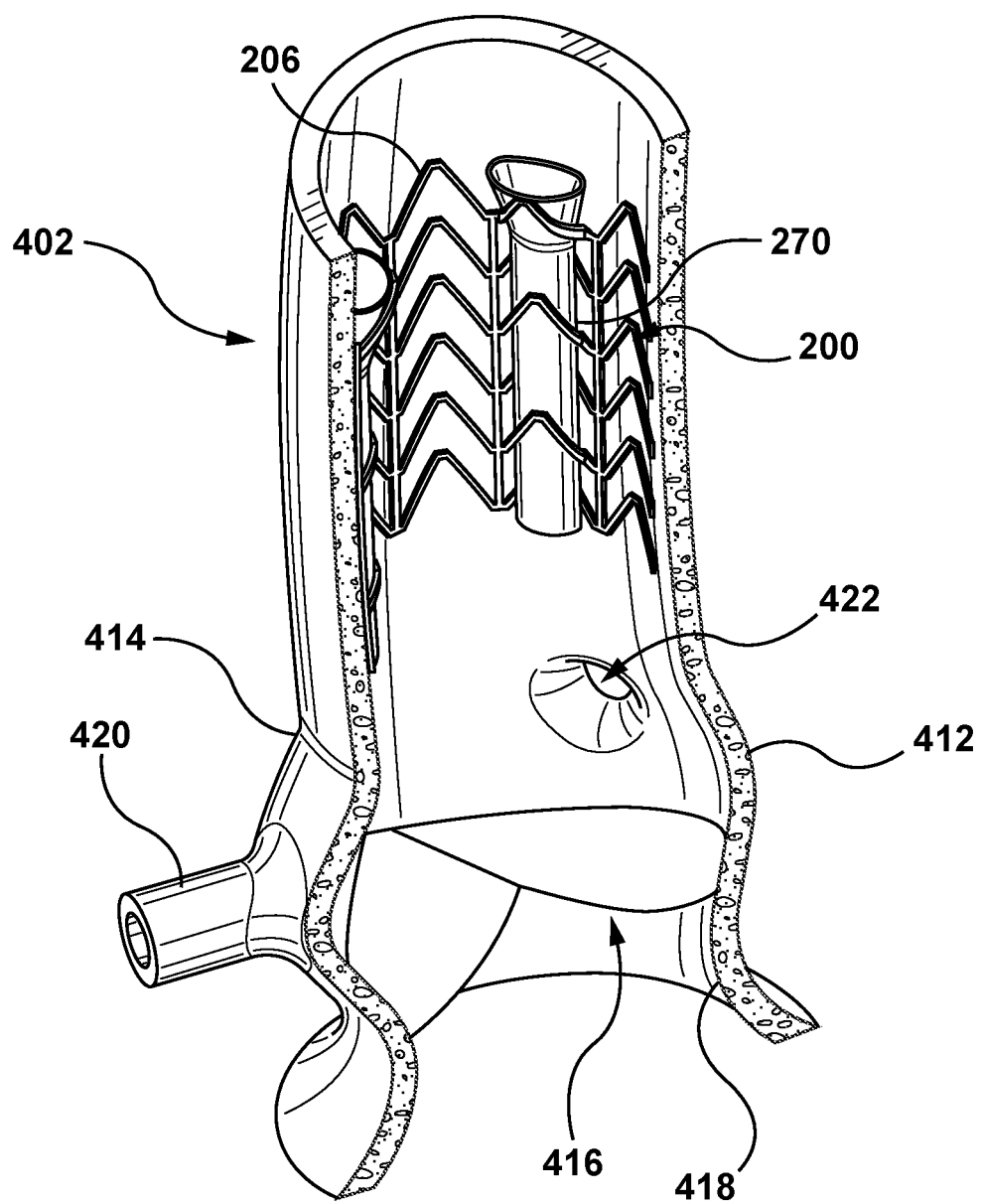

With anchor stent assembly 200 fully deployed, delivery system 500 may be retracted proximally, i.e., towards the clinician, and removed in a manner consistent with current procedures known to those in the art. Anchor stent assembly 200 remains in the fully deployed configuration with extension tubes 270 generally rotationally aligned with, but not obstructing coronary ostia 422, as shown in FIG. 8.

Figure 9:
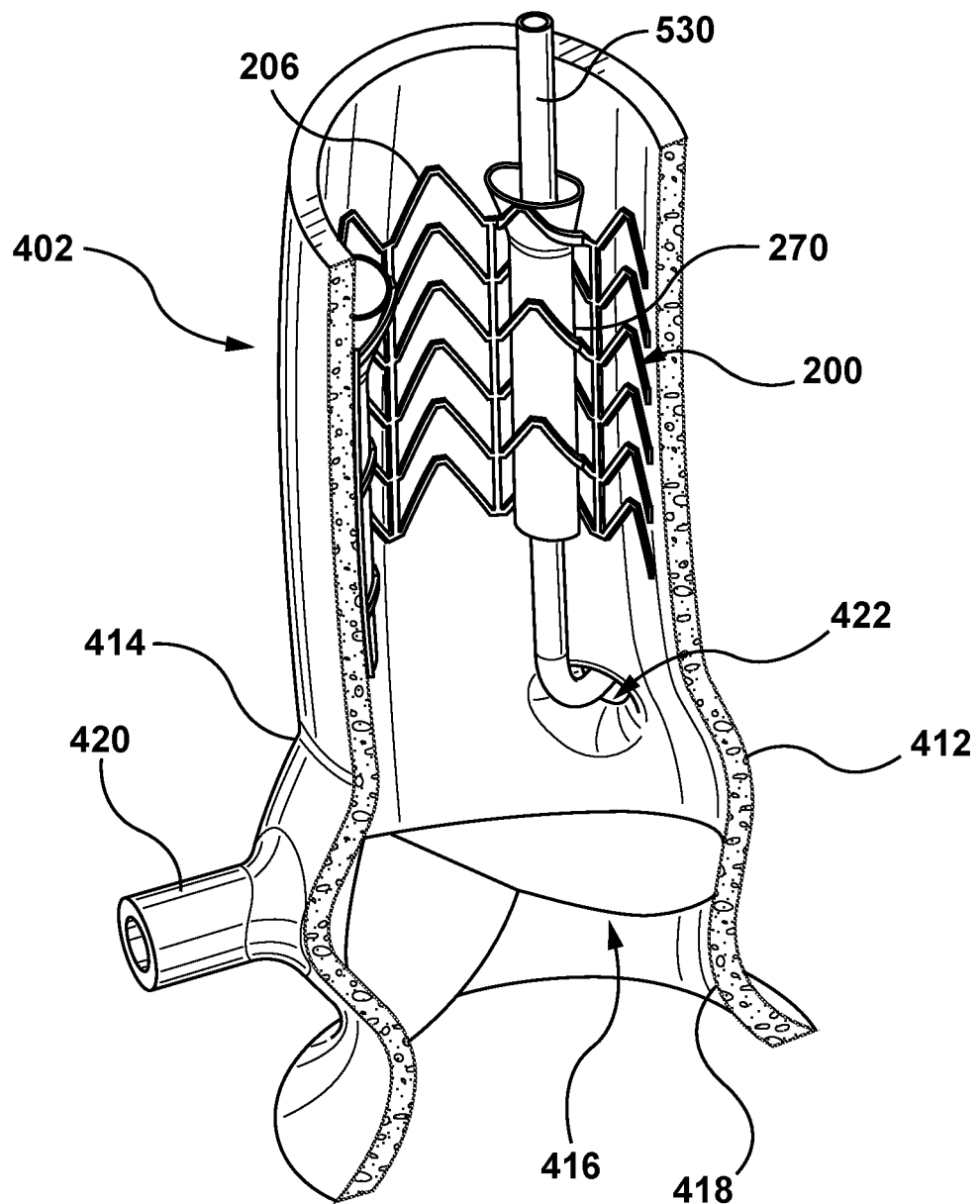

A steerable catheter 530 is advanced distally, i.e., away from the clinician and into one of extension tubes 270, as shown in FIG. 9. Steerable catheter 530 is guided into and through extension tube 270 and into coronary ostium 422 and coronary artery 420. Guidance may occur from one of several methods including, but not limited to, x-ray fluoroscopy, ultrasound imaging, electromagnetic tracking, radiopaque markers, or other methods suitable for the purposes disclosed herein.

Figure 10:
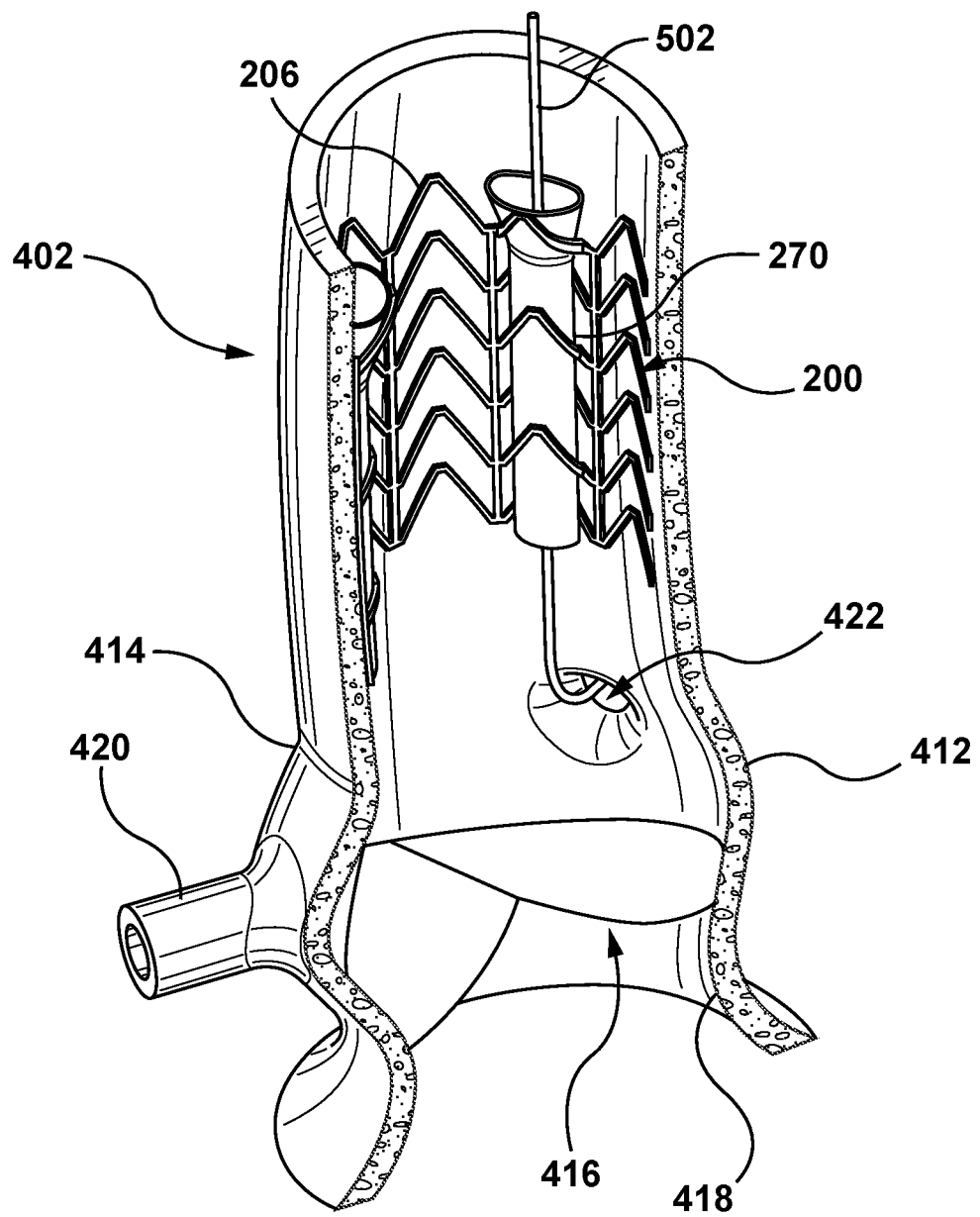

Once in place within extension tube 270 and coronary artery 420, a guidewire 502 is extended through catheter 530. With guidewire 502 positioned through extension tube 270 and into coronary artery 420, steerable catheter 530 is retracted proximally, i.e., toward the clinician, and removed in a manner consistent with current procedures known to those in the art. Guidewire 502 remains disposed through extension tube 270 and into coronary artery 420, as shown in FIG. 10.

Figure 11:
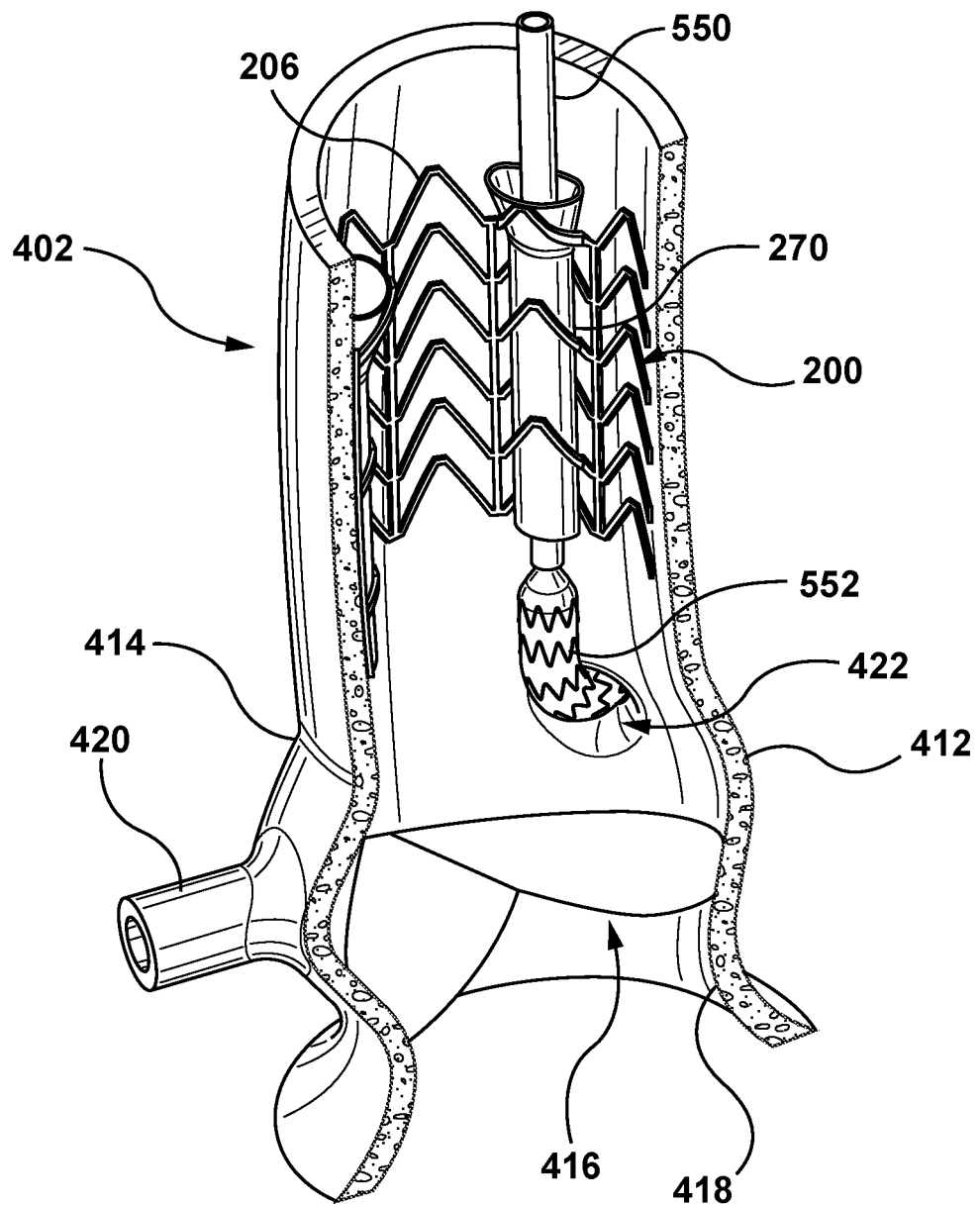

A coronary stent delivery system 550 for delivering a coronary stent 552 is advanced distally, i.e., away from the clinician, over guidewire 502 to a location in the coronary artery 420 via coronary ostium 422, as shown in FIG. 11. Delivery system 550 may be any suitable delivery system for delivering coronary stents and/or stent grafts as is known in the art. In the embodiment shown schematically, coronary stent 552 is a balloon-expandable stent including a graft (i.e., a balloon-expandable stent graft), but other types of stents may be used (e.g., self-expanding, uncovered, etc.). Accordingly, delivery system 550 generally may include a guidewire shaft (not shown), a distal tip (not shown), and a balloon (not shown) on which coronary stent 552 is disposed in a radially compressed or delivery configuration during intraluminal delivery, as shown in FIG. 11. Coronary stent delivery system 550 may also include other features, for example, radiopaque markers such that the clinician may determine when delivery system 550 and/or coronary stent 552 is in the proper location for deployment.

Figure 12:
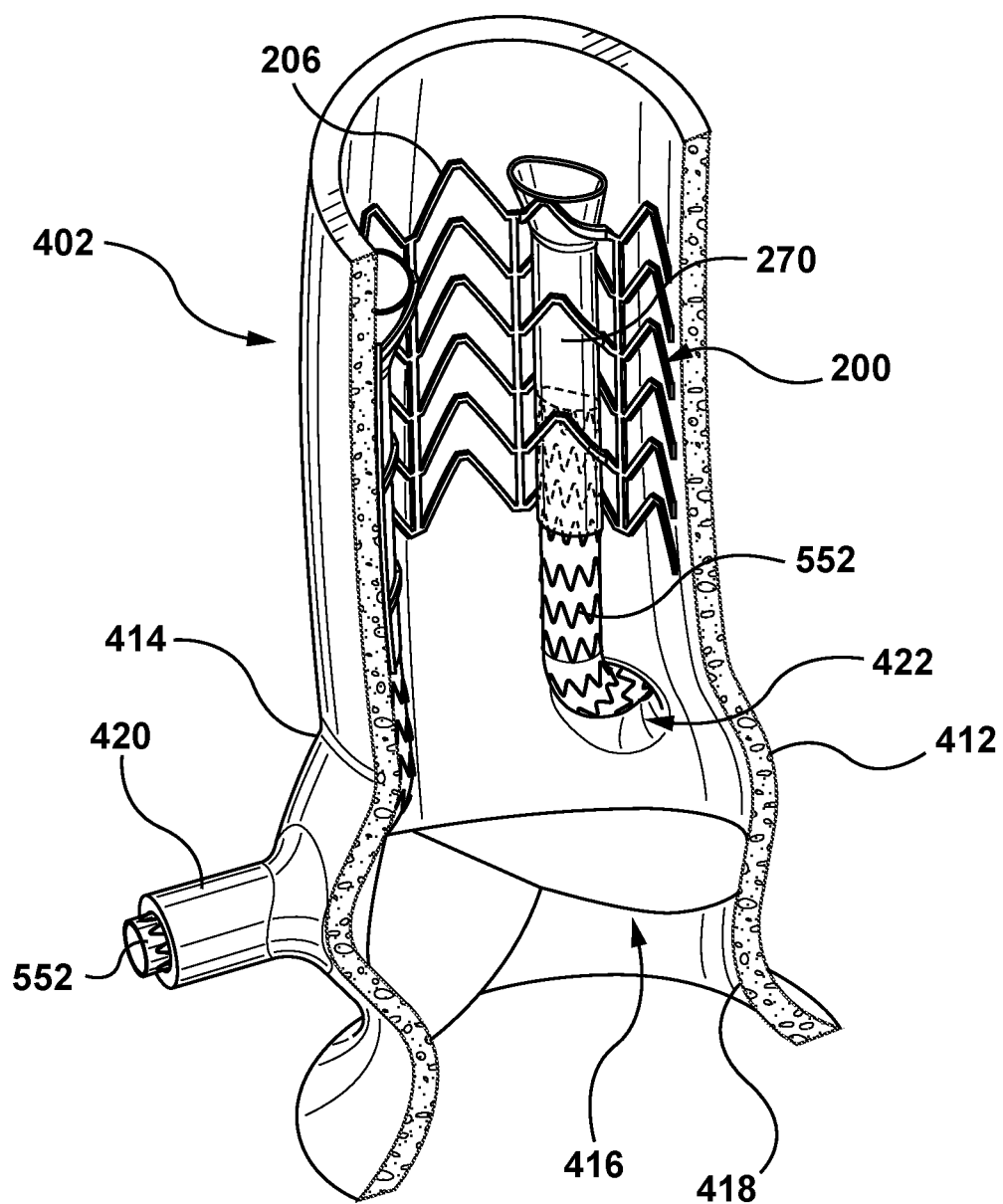

Once delivery system 550 has been advanced to the desired location, the balloon is inflated, causing coronary stent 552 to expand radially outward, engaging the inner wall of extension tube 270 and inner wall of coronary artery 420, as shown in FIG. 12. Coronary stent delivery system 550 is retracted proximally, i.e., toward the clinician, and removed in a manner consistent with procedures known to those in the art. The same method described above is repeated for the other coronary artery 420 to deliver and deploy a second coronary stent 552. Thus, in FIG. 12, two coronary stents 552 are shown deployed partially within a respective coronary artery 420 and partially within a respective extension tube 270.

Figure 13:
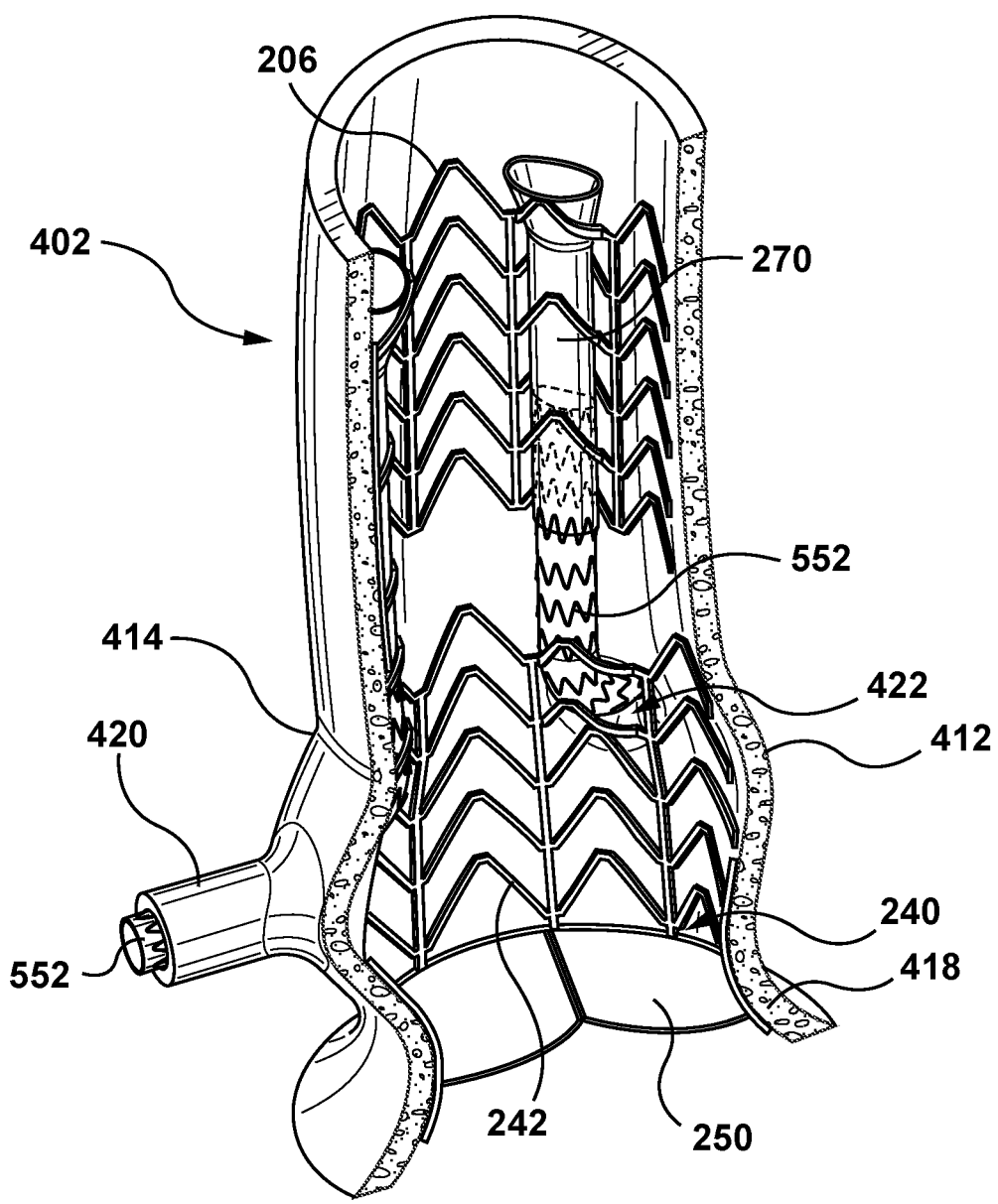

Valve component 240 may now be delivered and deployed at the native aortic valve 416 using methods and procedures known in the art. As shown in FIG. 13, valve component 240 may include a prosthetic valve 250 disposed within valve a frame 242. As also shown in FIG. 13, frame 242 of valve component 240 may overlap with ostia 422 of the coronary arteries 420 without being concerned with blocking flow to the coronary arteries. This is so because blood flow to the coronary arteries flows through extension tubes 270 and coronary stents 552 into coronary arteries 420. This also provides an increased landing zone for the valve component. Any location between the annulus and before which the native valve leaflets are no longer captured by the valve frame is a valid landing zone for the proximal (i.e., inflow) end of the valve frame. Thus, the valve frame could be placed farther away from the annulus which may result in less incidence of heart block. Further, a fully skirted valve component may be used, which may result in less paravalvular leakage (PVL), without blocking flow to the coronary arteries. Further, if future procedures are required in a coronary artery (balloon angioplasty, stent placement, etc.), access to the coronary arteries may be achieved through the coronary stents 552. Further, although not shown in FIG. 13, frame 242 of valve component 240 may extend into the ascending aorta such that frame 242 is disposed within central passage 208 of frame 206 of anchor stent 202, as explained in more detail in U.S. Patent Application Publication No. 2015/0119974 assigned to Medtronic, Inc., the contents of which are incorporated by reference herein in their entirety.

FIGS. 14-19 show schematically a method of delivering and deploying anchor stent assembly 300 of FIG. 4B and a valve component. FIGS. 14-19 are not drawn to scale regarding relative lengths of anchor stent assembly 300 and valve component 240.

Figure 14:
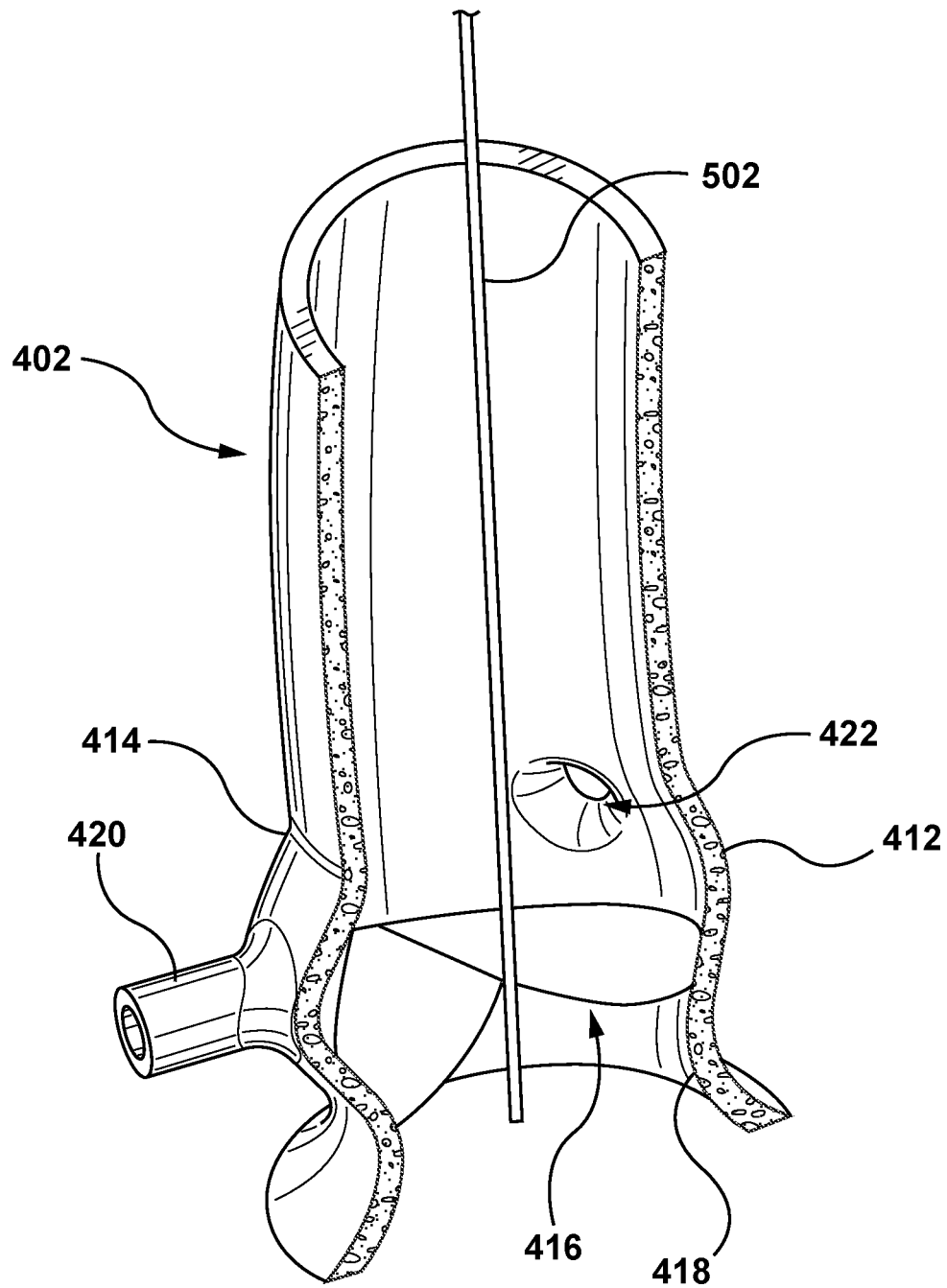
FIGS. 14-19 are schematic illustrations of an embodiment of a method for delivering and deploying a valve prosthesis at a native aortic valve with the anchor stent assembly of FIG. 4B deployed in the aorta above the aortic sinuses.

Similar to the description above, guidewire 502 is advanced distally, i.e., away from the clinician, through the aorta 400, past the sinotubular junction 414, and into the aortic sinuses 412 in the region of the aortic valve 416 and annulus 418, as shown in FIG. 14. Guidewire 502 may be introduced through an opening or arteriotomy through the wall of femoral artery in the groin region of the patient by methods known to those skilled in the art, such as, but not limited to, the Seldinger technique. Guidewire 502 is advanced into the descending (or abdominal) aorta (not shown), the aortic arch (not shown), and the ascending aorta 402, as shown in FIG. 14. Although FIGS. 14-19 show a retrograde percutaneous femoral procedure, it is not meant to limit the method of use and other procedural methods may be used. For example, and not by way of limitation, retrograde percutaneous implantation via subclavian/axillary routes, direct apical puncture, and the use of direct aortic access via either ministernotomy or right anterior thoracotomy may also be used.

Figure 15:
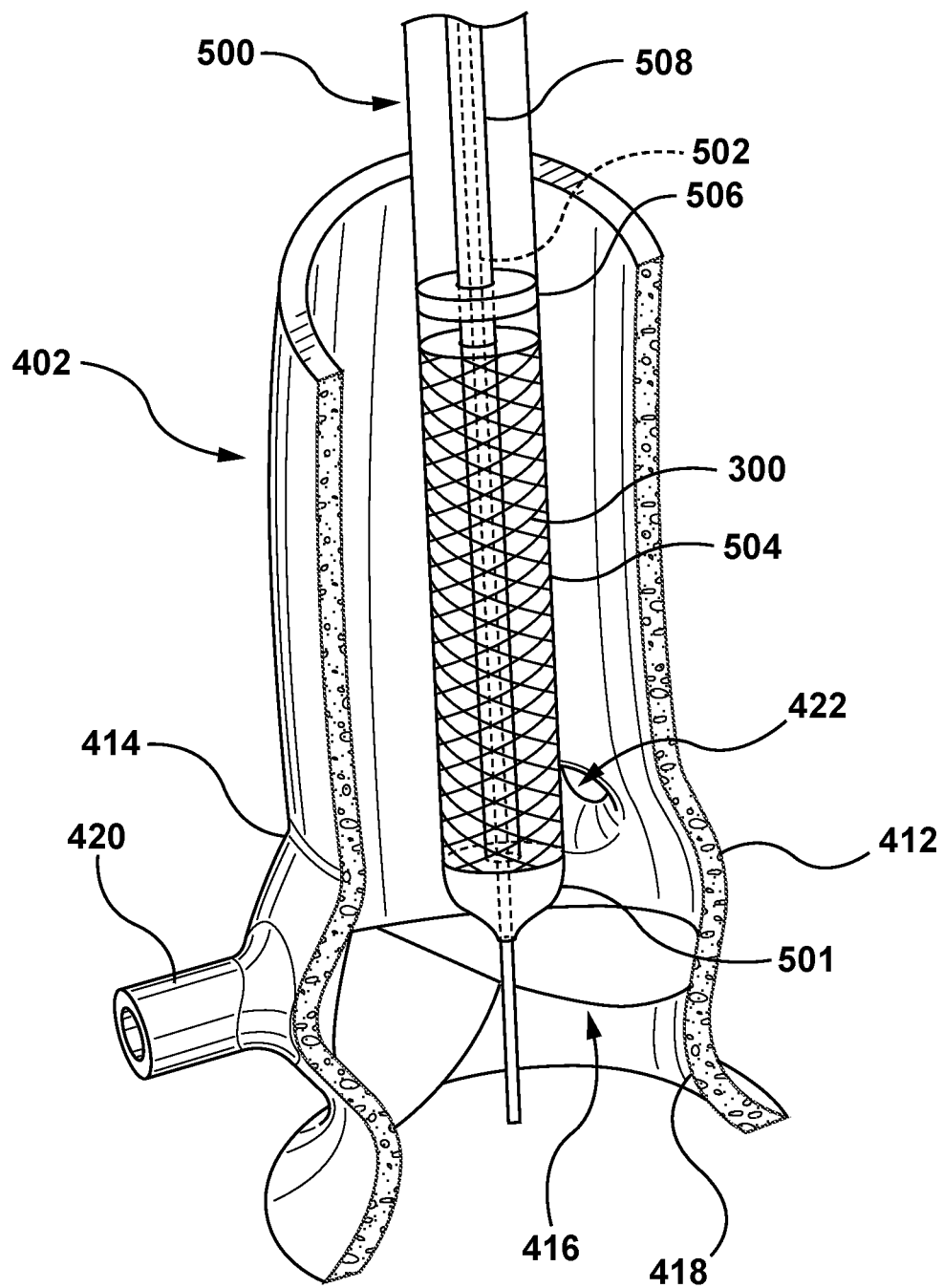

A delivery system 500 for delivering anchor stent assembly 300 being advanced distally, i.e., away from the clinician, over guidewire 502 to a location in the aortic sinuses 412, as shown in FIG. 15. Delivery system 500 may be any suitable delivery system for delivering stents and/or stent grafts. In the embodiment shown schematically, anchor stent 302 of anchor stent assembly 300 is a self-expanding stent. Accordingly, delivery system 500 generally includes an inner or guidewire shaft 508, which includes a guidewire passage (not shown) for receiving guidewire 502. A proximal end of guidewire 502 may be back loaded into the guidewire passage (not shown) of inner shaft 508 through a distal opening (not shown) in inner shaft 508. Delivery system 500 may be an over-the-wire type catheter, or a rapid exchange catheter, or other catheter devices. Delivery system 500 further generally may include a distal tip 501, an outer sheath 504 that maintains anchor stent 302 in the radially compressed or delivery configuration during intraluminal delivery through the vasculature, as shown in FIG. 15, and may also include a pusher or stopper 506, and other features. Delivery system 500 and/or anchor stent assembly 300 may also include, for example, radiopaque markers such that the clinician may determine when delivery system 500 and/or anchor stent assembly 300 is in the proper location and alignment for deployment.

Figure 16:
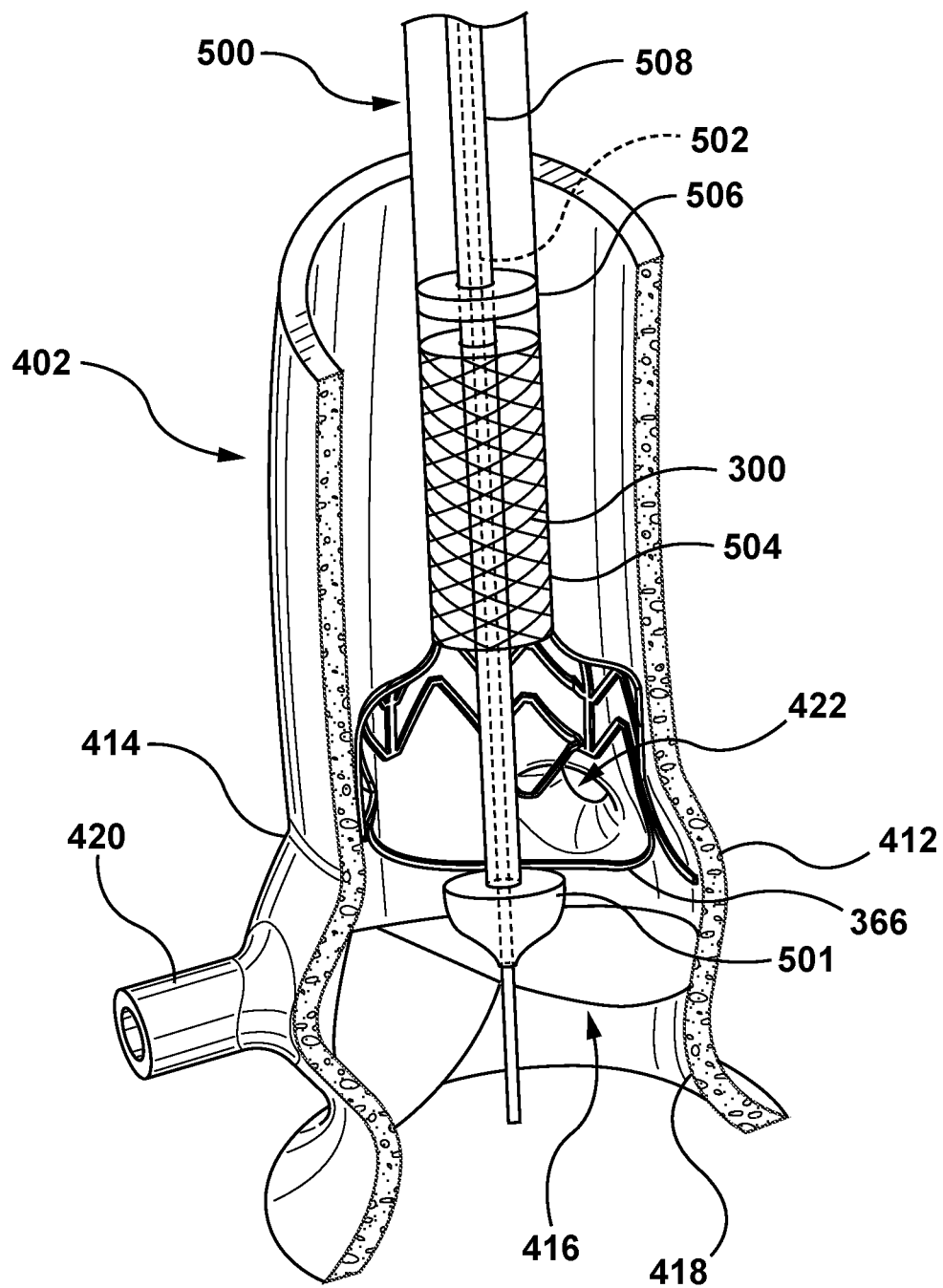

Once delivery system 500 has been advanced to the desired location, such as when first end 312 of frame 306 of anchor stent 302 is generally aligned with sinotubular junction 414, and proximal alignment arms 364 and 366 are rotationally aligned with and encircle, but do not obstruct, coronary ostia 422, outer sheath 504 is retracted proximally, i.e., towards the clinician, as shown in FIG. 16. As outer sheath 504 is retracted, proximal alignment arms 362 (not shown), 364 (not shown), and 366 engage the inner wall of the aortic sinuses 412, and frame 306 of anchor stent 302 expands radially outward, engaging the inner wall of ascending aorta 402, as shown in FIG. 16.

Outer sheath 504 is further retracted proximally, i.e., towards the clinician, to complete deployment of anchor stent assembly 300 from outer sheath 504. In other words, sheath 504 is retracted such that anchor stent assembly 300 is no longer constrained by sheath 504.

Figure 17:
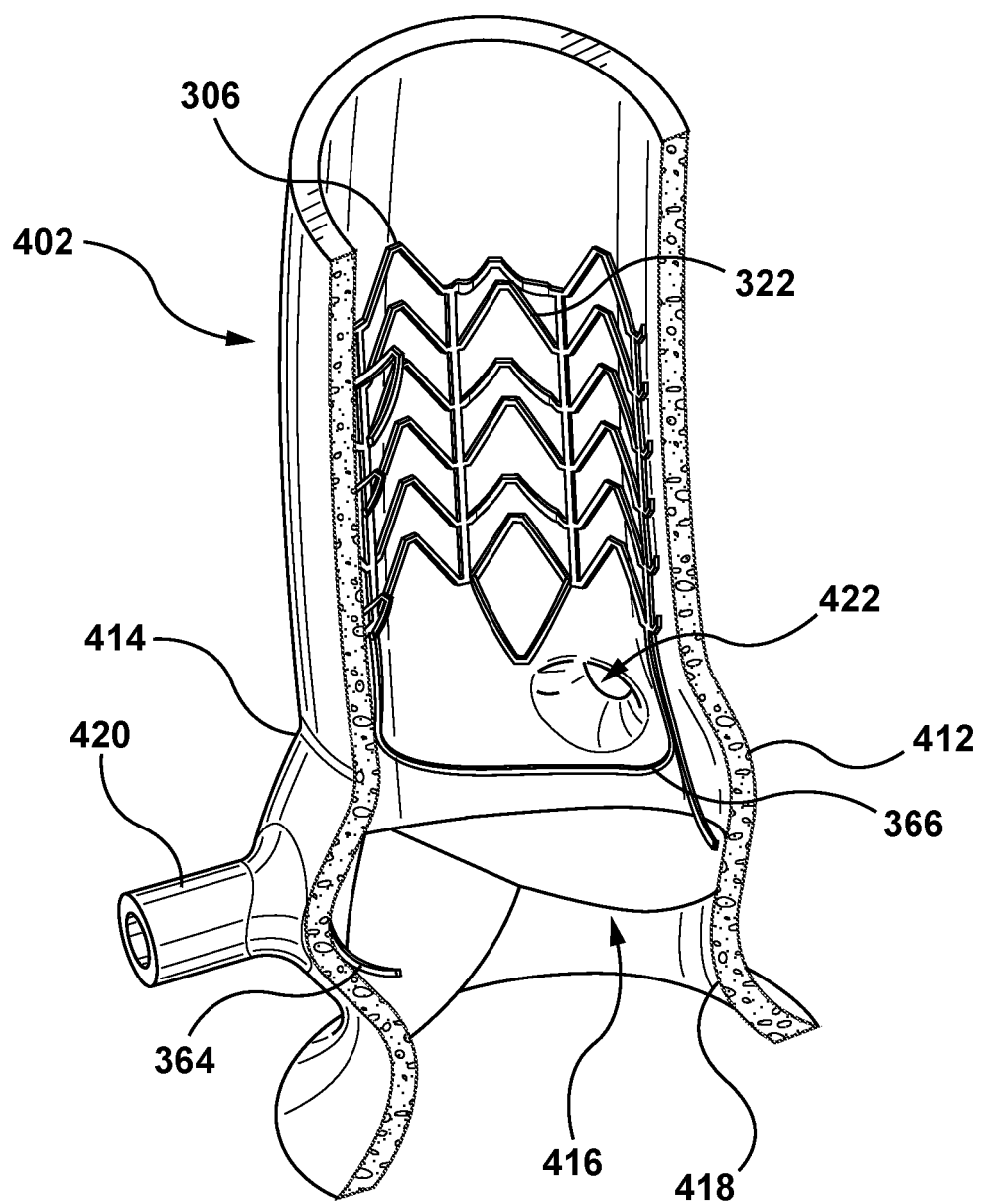
Figure 18:
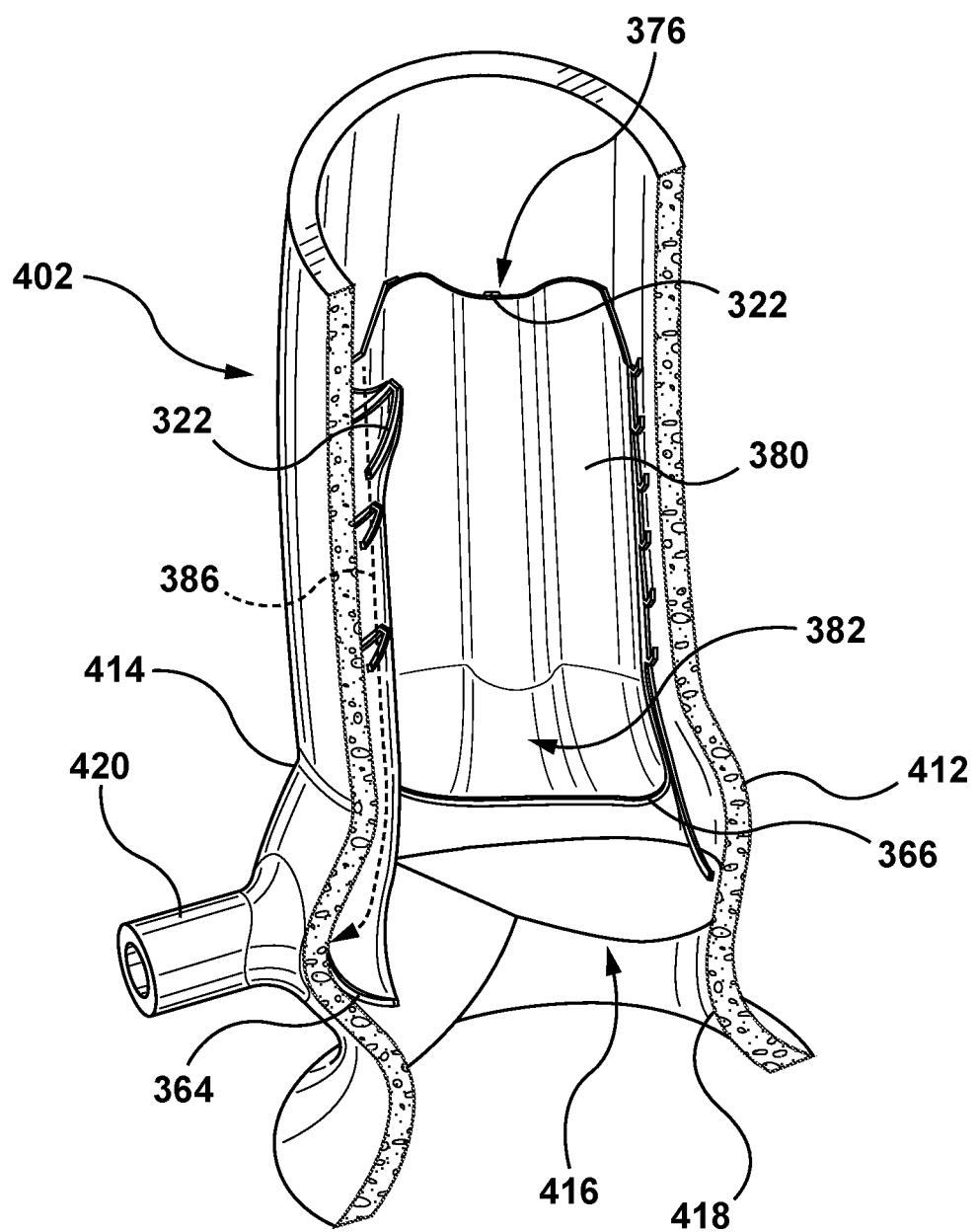

With anchor stent assembly 300 fully deployed, delivery system 500 may be retracted proximally, i.e., towards the clinician, and removed in a manner consistent with procedures known to those in the art. Anchor stent assembly 300 remains in the fully deployed configuration such that extension channels 321$a$/321$b$ are generally rotationally aligned with respective coronary ostia 422 and proximal arms 364 and 366 encircle, but do not obstruct coronary ostia 422, as shown in FIG. 17 (with skirt removed for clarity) and FIG. 18 (with skirt 380 in place). Skirt 380, when anchor stent assembly 300 is in the expanded deployed configuration, defines extension channels 321 and coronary pockets 382 between an outer surface of skirt 380 and the inner surface of the wall of the ascending aorta/aortic sinuses, providing unrestricted blood flow to coronary artery 420, as indicated by coronary blood flow direction arrow 386 of FIG. 18. Because coronary pockets 283 are relatively large, extension channels 321$a$/321$b$ do not need to be perfectly rotationally aligned with the corresponding coronary ostia 422 and blood will still funnel to the coronary ostia 422 and into the coronary artery 420.

Figure 19:
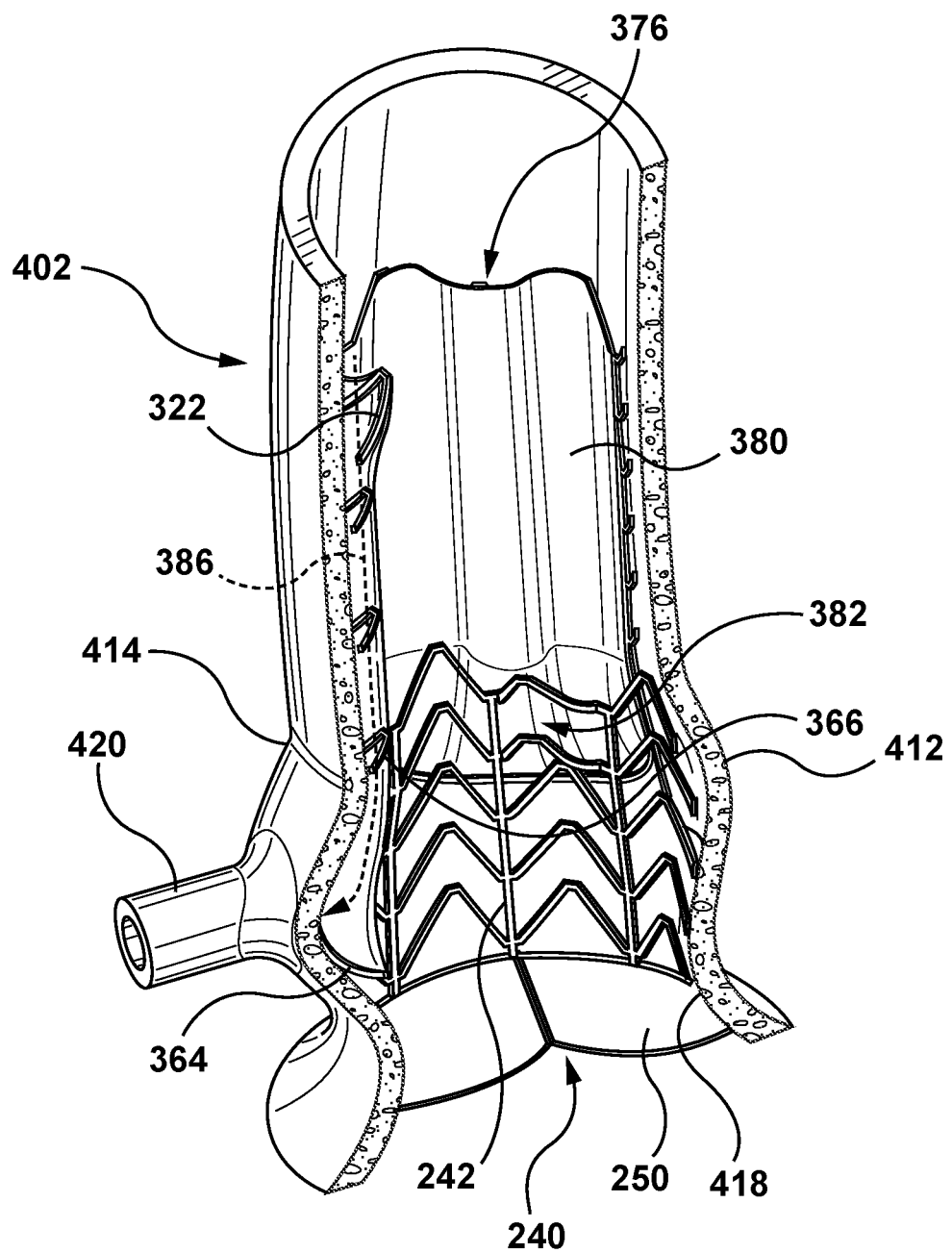

Valve component 240, as described above, may now be delivered and deployed at the native aortic valve 416 using methods and procedures known in the art. Once in place, prosthetic valve 350 resides within valve frame 342 at annulus 418 as shown in FIG. 19. As also shown in FIG. 13, frame 242 of valve component 240 may overlap with ostia 422 of the coronary arteries 420 without being concerned with blocking flow to the coronary arteries. This is so because blood flow to the coronary arteries flows through extension channels 321$a$/321$b$ and coronary pockets 382 into coronary arteries 420. This also provides an increased landing zone for the valve component. Any location between the annulus and before which the native valve leaflets are no longer captured by the valve frame is a valid landing zone for the proximal (i.e., inflow) end of the valve frame. Thus, the valve frame could be placed farther away from the annulus which may result in less incidence of heart block. Further, a fully skirted valve component may be used, which may result in less paravalvular leakage (PVL), without blocking flow to the coronary arteries. Further, if future interventional procedures are required in a coronary artery (balloon angioplasty, stent placement, etc.), access to the coronary arteries may be achieved through extension channels 321. Further, although not shown in FIG. 19, frame 242 of valve component 240 may extend into the ascending aorta such that frame 242 is disposed within central passage 308 of frame 306 of anchor stent 302, as explained in more detail in U.S. Patent Application Publication No. 2015/0119974 assigned to Medtronic, Inc., the contents of which are incorporated by reference herein in their entirety.

Figure 20A:
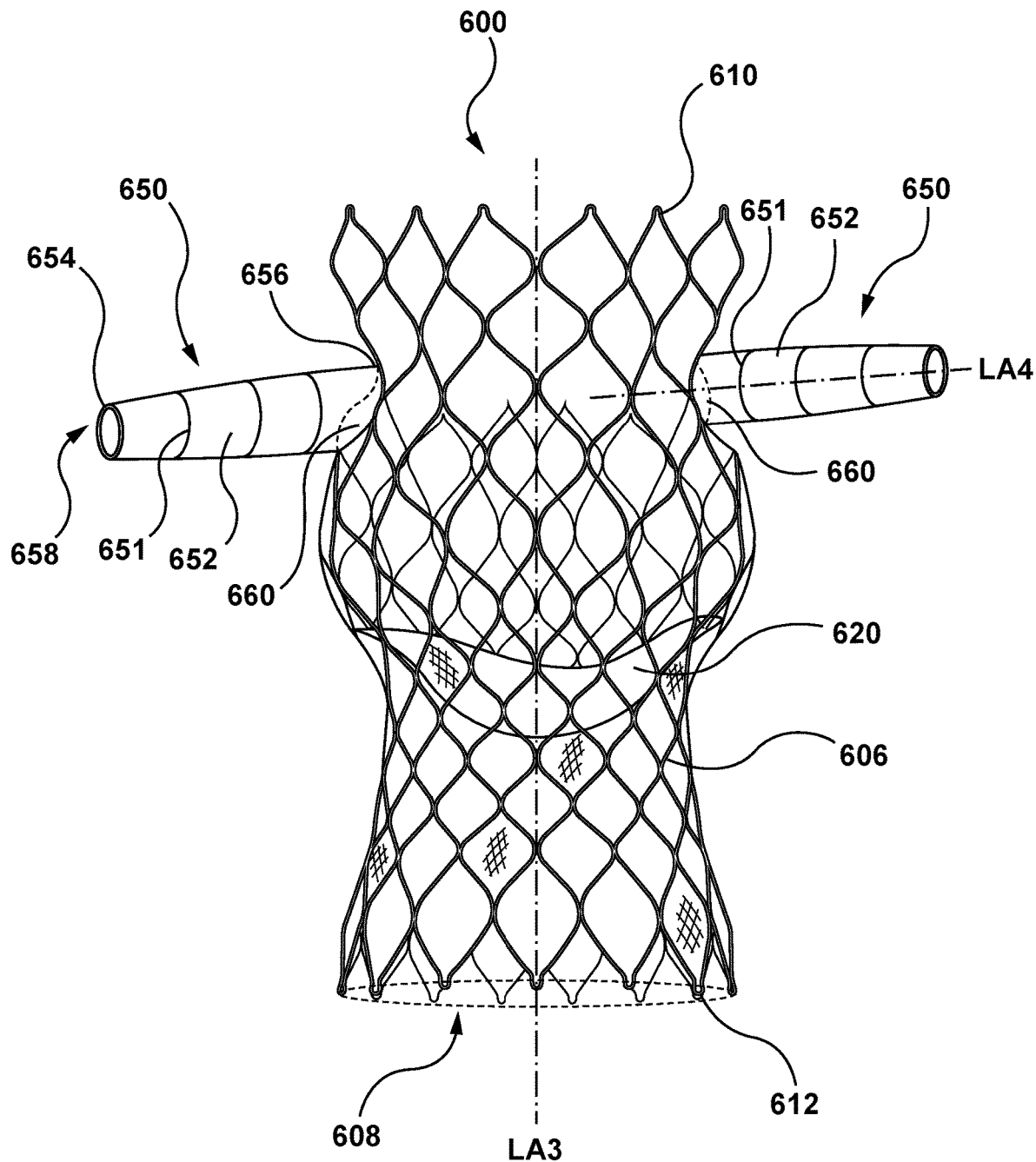
FIGS. 20A-20B are schematic illustrations of a valve prosthesis in accordance with another embodiment hereof.
Figure 20B:
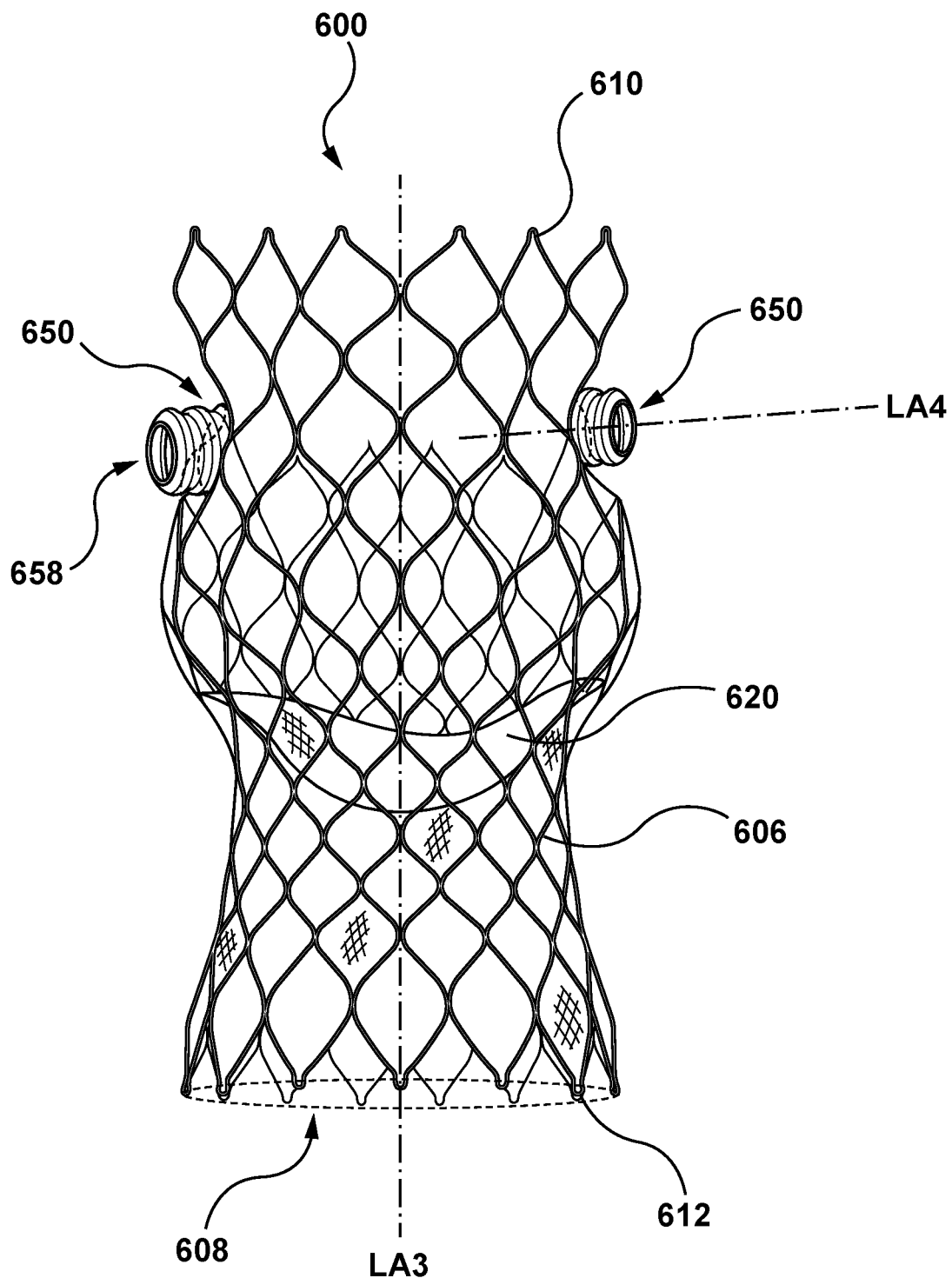

FIGS. 20A and 20B show an embodiment of an integrated valve assembly 600 including a frame 606, a prosthetic valve 620, and coronary arms 650. Valve assembly 600 is sized and designed to deploy within the aortic sinuses and annulus of a heart, as described in more detail below.

Frame 606 includes a first end 612 and a second end 610, as shown in FIGS. 20A and 20B. Frame 606 is a generally tubular configuration having a central passage 608 and a central longitudinal axis LA3. Frame 606 is a stent structure as is known in the art and may be self-expanding. Frame 606 a coronary orifice 660 between an inner surface and an outer surface of frame 606. Coronary orifice 660 is an opening through the wall of frame 606. Coronary orifice 660 may be a separate opening or may be an opening defined by cells in frame 606. Coronary orifice 660 is described in more detail below in the description of coronary arms 650. Generally, frame 606 includes a first, radially compressed configuration for delivery and a second, radially expanded or deployed configuration when deployed at the desired site. Frame 606 is a collapsible structure and may be constructed of materials such as, but not limited to, stainless steel, Nitinol, cobalt-chromium alloys, or other suitable materials for the purposes disclosed herein.

Each coronary arm 650 is a generally tubular structure, defining a longitudinal passage 658 with a longitudinal axis LA4. Longitudinal axis LA4 is generally transverse to longitudinal axis LA3. Although longitudinal axis LA4 has been defined with respect to one of the coronary arms 650, those skilled in the art would recognize that the coronary arms do not need to align with each other. Instead, coronary arms 650 extend from frame 606 at locations such that coronary arms 650 can extend into a respective coronary artery, as described in more detail below. Thus, coronary arms 650 may be longitudinally offset, if appropriate. Coronary arms 650 may include struts 651 coupled to graft material 652, similar to a stent-graft construction. Struts 651 may be any suitable material generally used in stent, such as, but not limited to, stainless steel or Nitinol. Struts 651 may be the same material as frame 606. Graft material 652 may be any suitable material generally used for a graft such as, but not limited to, woven polyester such as polyethylene terephthalate, polytetrafluoroethylene (PTFE), other polymers, or other biocompatible materials. Graft material 652 and struts 651 may be coupled by sutures, fusion, or other coupling methods known in the art. Further, graft material 652 may be coupled to the outer surface or inner surface of struts 651. Coronary arms 650 may be coupled to frame 606 by fusion, laser or ultrasonic welding, mechanical connections such as sutures, or other methods suitable for the purposes disclosed herein. In another embodiment, struts 651 of coronary arms 650 may be constructed integrally with frame 606.

Coronary arms 650 have a first end 656 and a second end 654, and a longitudinally collapsed delivery configuration and a longitudinally extended deployed configuration. When in the longitudinally collapsed delivery configuration, second end 654 is adjacent to first end 656, as shown in FIG. 20B. When in the longitudinally extended deployed configuration, second end 654 is spaced from first end 656, as shown in FIG. 20A. Thus, as described, coronary arms 650 telescope from the longitudinally collapsed delivery configuration to the longitudinally extended deployed configuration. Coronary arms 650 may be of any length suitable for the purposes disclosed herein. For example, and not by way of limitation, coronary arms 650 may have a length in the range of 15 mm-300 mm.

Coronary arms 650 are configured such that the longitudinal axis of each coronary arm 650 generally aligns with a corresponding longitudinal axis of the coronary artery into which it is to be inserted.

While the embodiment of FIGS. 20A-20B shows telescoping coronary arms 650 as series of circular struts 651 coupled to graft material 652 to form concentrically connected cylinders, it is not meant to limit the design, and it is understood that other materials and configurations may be employed such that depending on the specific requirements of the components, devices, and procedures.

Prosthetic valve 620 may be any prosthetic valve. For example, and not by way of limitation, prosthetic valve 620 may be similar to valve body 104 described above with respect to FIGS. 1 and 2, or as described in the '765 publication. Prosthetic valve 620 is coupled to and disposed within frame 606 of valve assembly 600.

Figure 21:
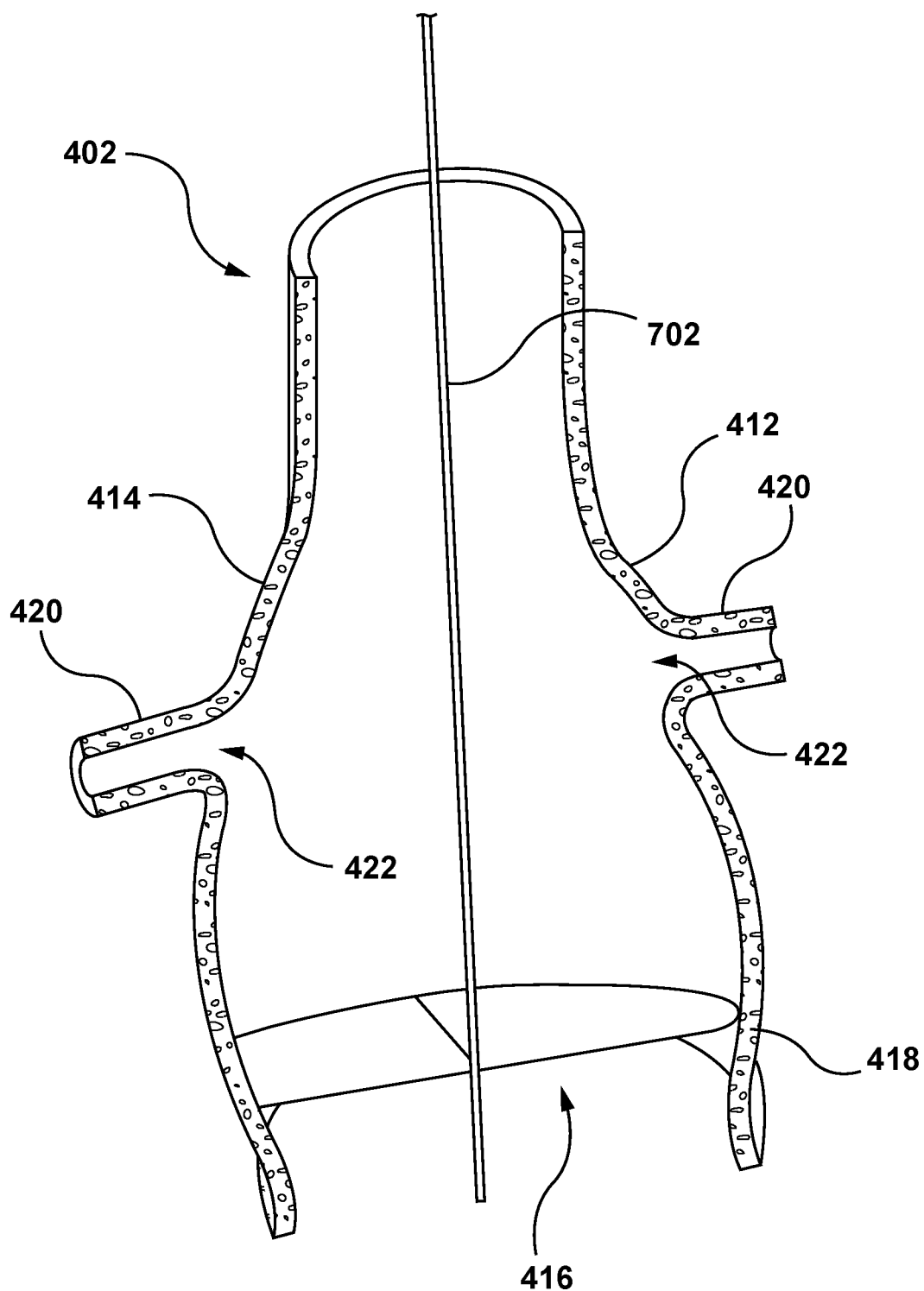
FIGS. 21-27 are schematic illustrations of an embodiment of a method for delivering and deploying the valve prosthesis of FIGS. 20A-20B at an aortic valve.

A method of delivering and deploying valve assembly 600 in accordance with an embodiment hereof is schematically represented in FIGS. 21-27. As shown in FIG. 21, a guidewire 702 advanced distally, i.e., away from the clinician, through the aorta 400, past the sinotubular junction 414, and into the aortic sinuses 412 in the region of the aortic valve 416 and annulus 418. Guidewire 702 may be introduced through an opening or arteriotomy through the wall of femoral artery in the groin region of the patient by methods known to those skilled in the art, such as, but not limited to, the Seldinger technique. Guidewire 702 is advanced into the descending (or abdominal) aorta (not shown), the aortic arch (not shown), and the ascending aorta 402, as shown in FIG. 21. Two coronary arteries 420 and their corresponding coronary ostia 422 are also shown in FIG. 21. Although FIGS. 21-27 show a retrograde percutaneous femoral procedure, it is not meant to limit the method of use and other procedural methods may be used. For example, and not by way of limitation, retrograde percutaneous implantation via subclavian/axillary routes, direct apical puncture, and the use of direct aortic access via either ministernotomy or right anterior thoracotomy may also be used.

Figure 22:
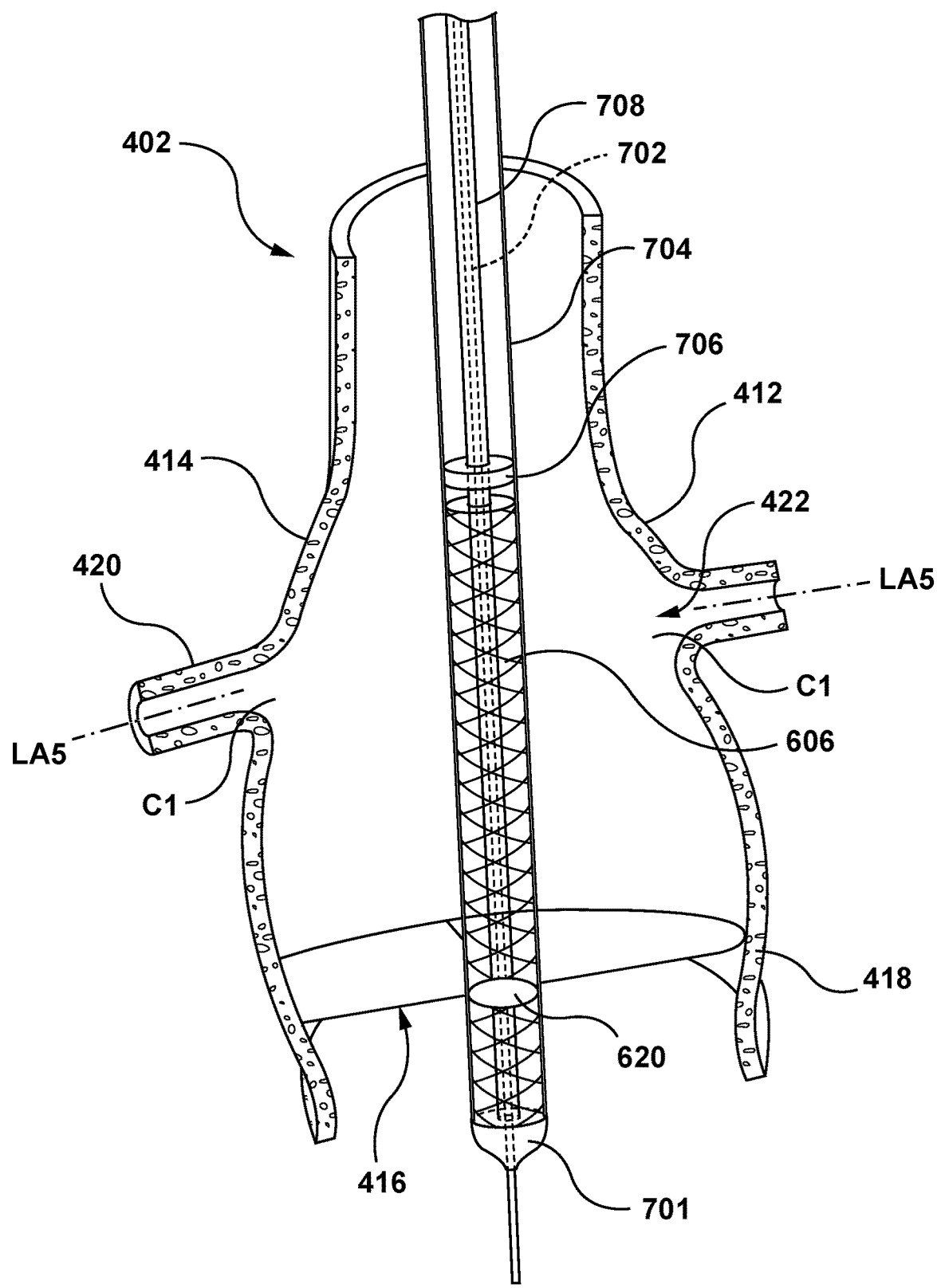

A delivery system 700 for delivering valve assembly 600 is advanced distally, i.e., away from the clinician, over guidewire 702 to a location at the annulus 418 of the heart, as shown in FIG. 22. Delivery system 700 may be any suitable delivery system for delivering stents and/or stent grafts. In the embodiment shown schematically, valve assembly 600 is a self-expanding frame 606. Accordingly, delivery system 700 generally includes an inner or guidewire shaft 708, which includes a guidewire passage (not shown) for receiving guidewire 702. A proximal end of guidewire 702 may be back loaded into the guidewire passage (not shown) of inner shaft 708 through a distal opening (not shown) in inner shaft 708. Delivery system 700 may be an over-the-wire type catheter, or a rapid exchange catheter, or other catheter devices. Delivery system 700 further generally may include a distal tip 701, an outer sheath 704 that maintains valve assembly 600 in the radially compressed or delivery configuration during intraluminal delivery through the vasculature, as shown in FIG. 22 and may also include a pusher or stopper 706, and other features. Delivery system 700 and/or valve assembly 600 may also include, for example, radiopaque markers such that the clinician may determine when delivery system 700 and/or valve assembly 600 is in the proper location and alignment for deployment.

Figure 23:
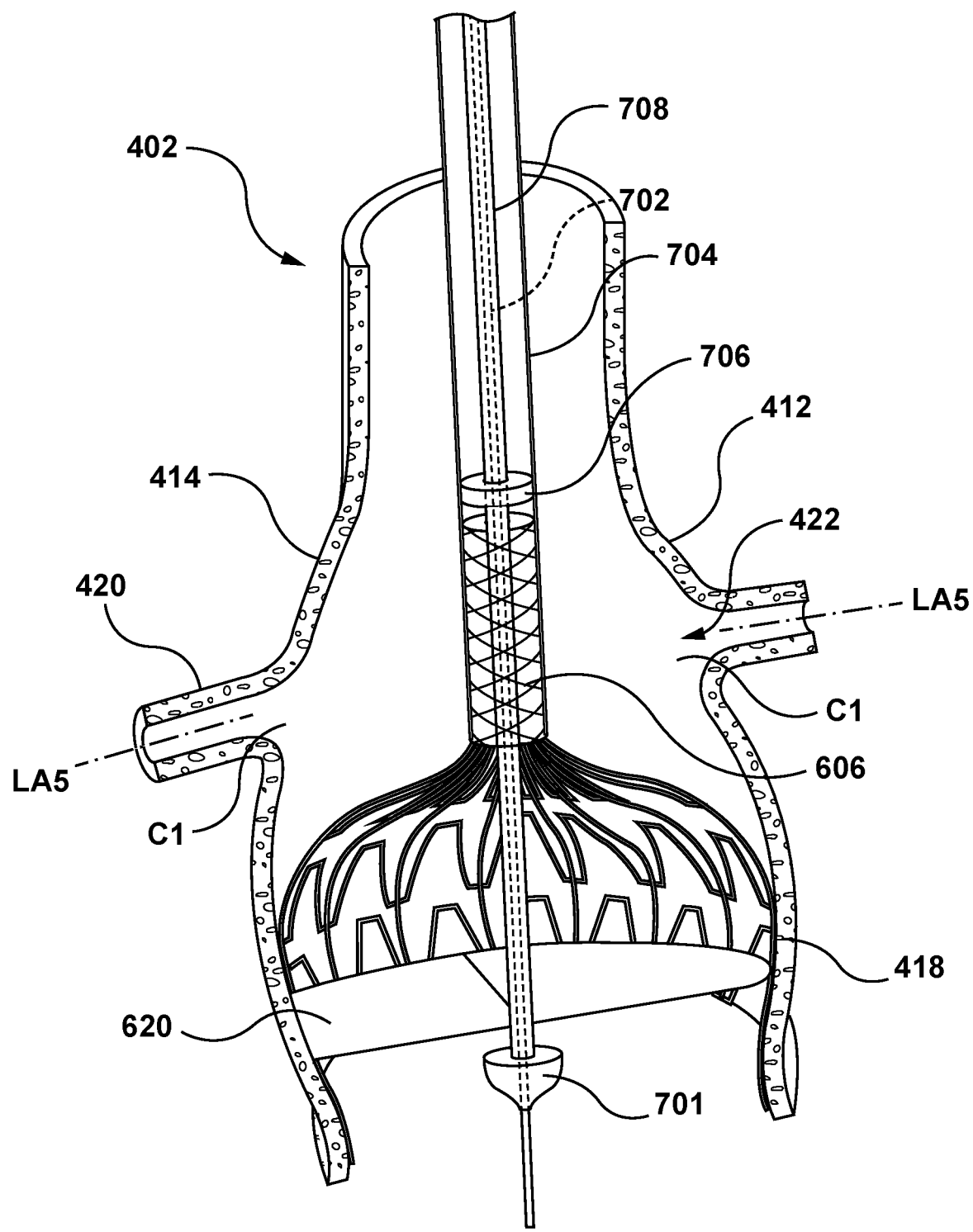

Once delivery system 700 has been advanced to the desired location such that each coronary arm 650 is generally rotationally and longitudinally aligned with the corresponding coronary ostium 422 of the corresponding coronary artery 420, outer sheath 704 is retracted proximally, i.e., towards the clinician, to deploy frame 606 of valve assembly 600, as shown in FIG. 23. As frame 606 expands radially outward, frame 606 separates the native leaflets of aortic valve 416.

Figure 24:
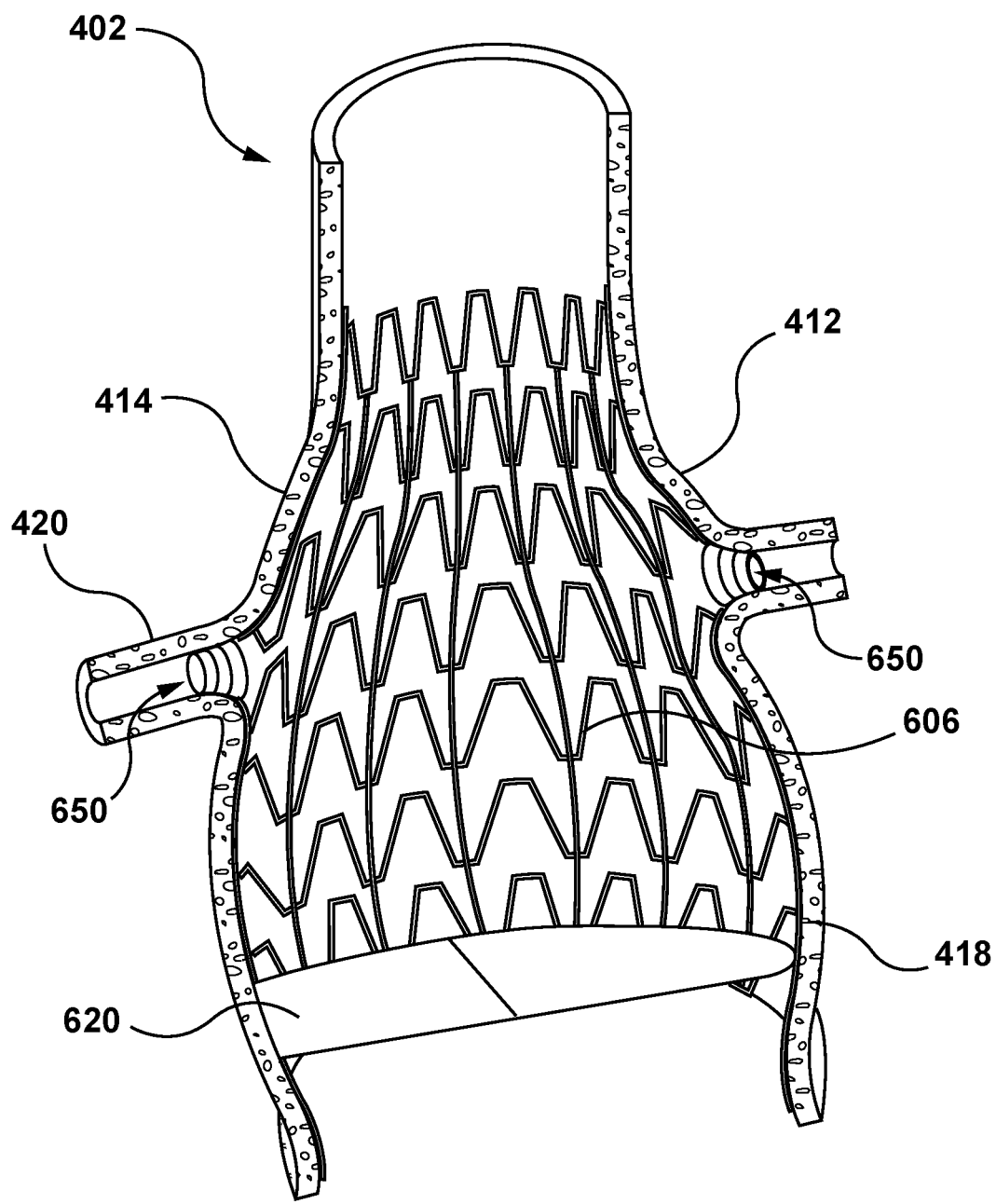

Outer sheath 704 is further retracted proximally, i.e., towards the clinician, to complete deployment of valve assembly 600 from outer sheath 704. Sheath 704 is retracted such that valve assembly 600 is no longer constrained by sheath 704 and expands radially outward, as shown in FIG. 24.

With valve assembly 600 fully deployed, delivery system 700 may be retracted proximally, i.e., towards the clinician, and removed in a manner consistent with procedures known to those in the art. Valve assembly 600 remains in the fully deployed configuration with coronary arms 650 in the longitudinally collapsed delivery configuration and aligned of the corresponding coronary arteries 420, as shown in FIG. 24.

Figure 25:
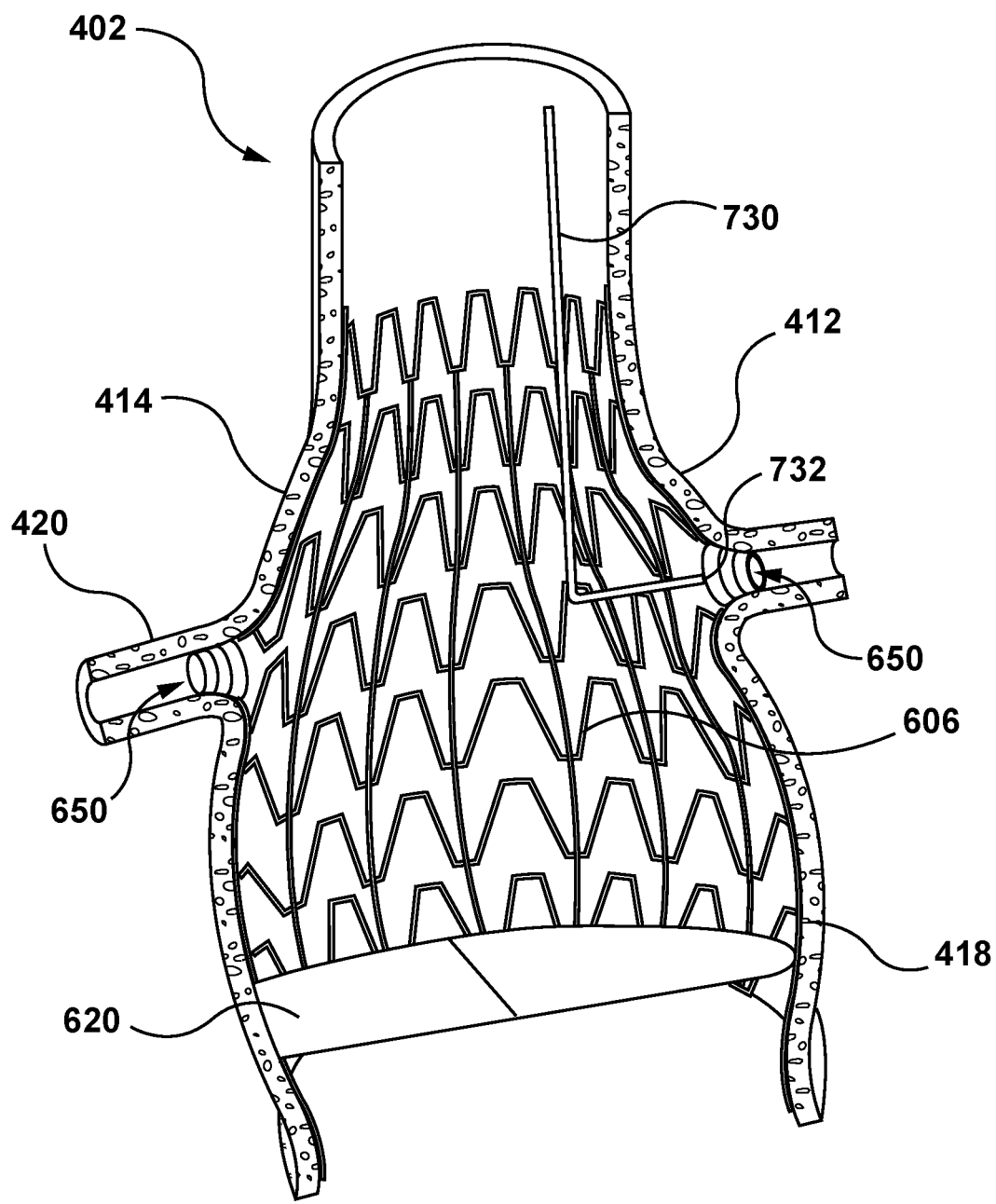

A steerable catheter or pushrod 730 is advanced distally, i.e., away from the clinician and into one coronary arms 650, as shown in FIG. 25. Pushrod 730 may be guided by x-ray fluoroscopy, ultrasound imaging, electromagnetic tracking, radiopaque markers, or other methods suitable for the purposes disclosed herein.

Figure 26:
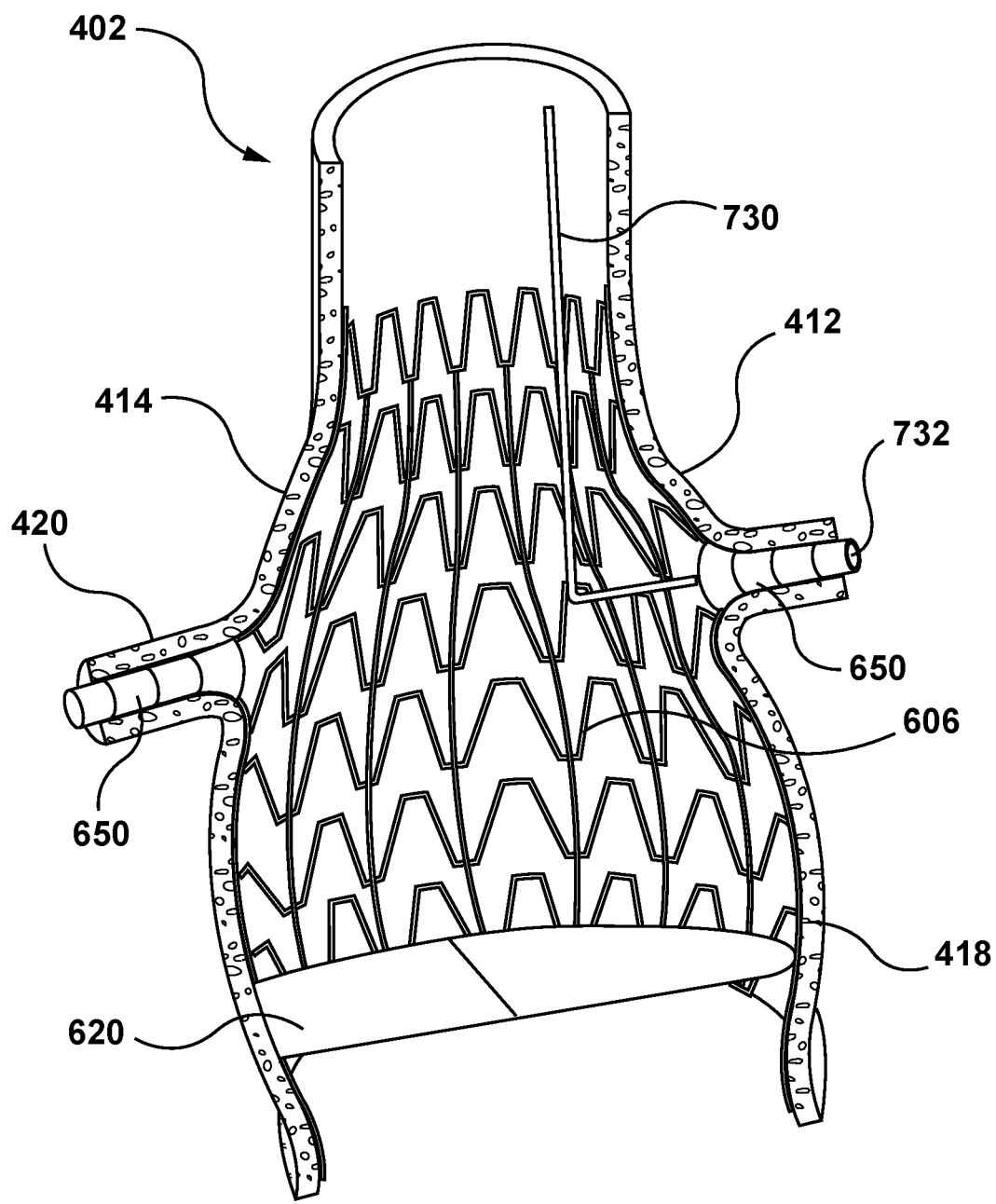

Once in place within telescoping coronary arm 650, pushrod 730 is advanced distally i.e., away from the clinician, such that distal end 732 of pushrod 730 engages second end 654 of coronary arm 650 and pushes second end 654 of coronary arm 650. Pushrod 730 continues to be advanced to extend second end 654 of coronary arm 650 into coronary artery 420, thereby deploying coronary arm 650 from its longitudinally collapsed delivery configuration to its longitudinally extended deployed configuration, as shown in FIG. 26. In another embodiment, a pushrod may be part of delivery system 700 such that a separate pushrod is not needed.

Once coronary arm 650 is in its longitudinally extended deployed configuration with second end 654 of coronary arm 650 disposed within coronary artery 420, steerable catheter 730 is retracted proximally, i.e., toward the clinician, and removed in a manner consistent with procedures known to those in the art. The procedure is repeated for the other coronary arm 650.

In another embodiment, coronary arms 650 may be formed of shape memory material such that they are self-extending. Accordingly, the pre-formed shape of each coronary arm 650 is the longitudinally extended deployed configuration. The coronary arms 650 are collapsed to the longitudinally collapsed delivery configuration when loaded into outer sheath 704. When outer sheath 704 is retracted, as described above, coronary arms 650 return to their pre-formed, longitudinally extended configuration without the use of the pushrod 730 described above.

Figure 27:
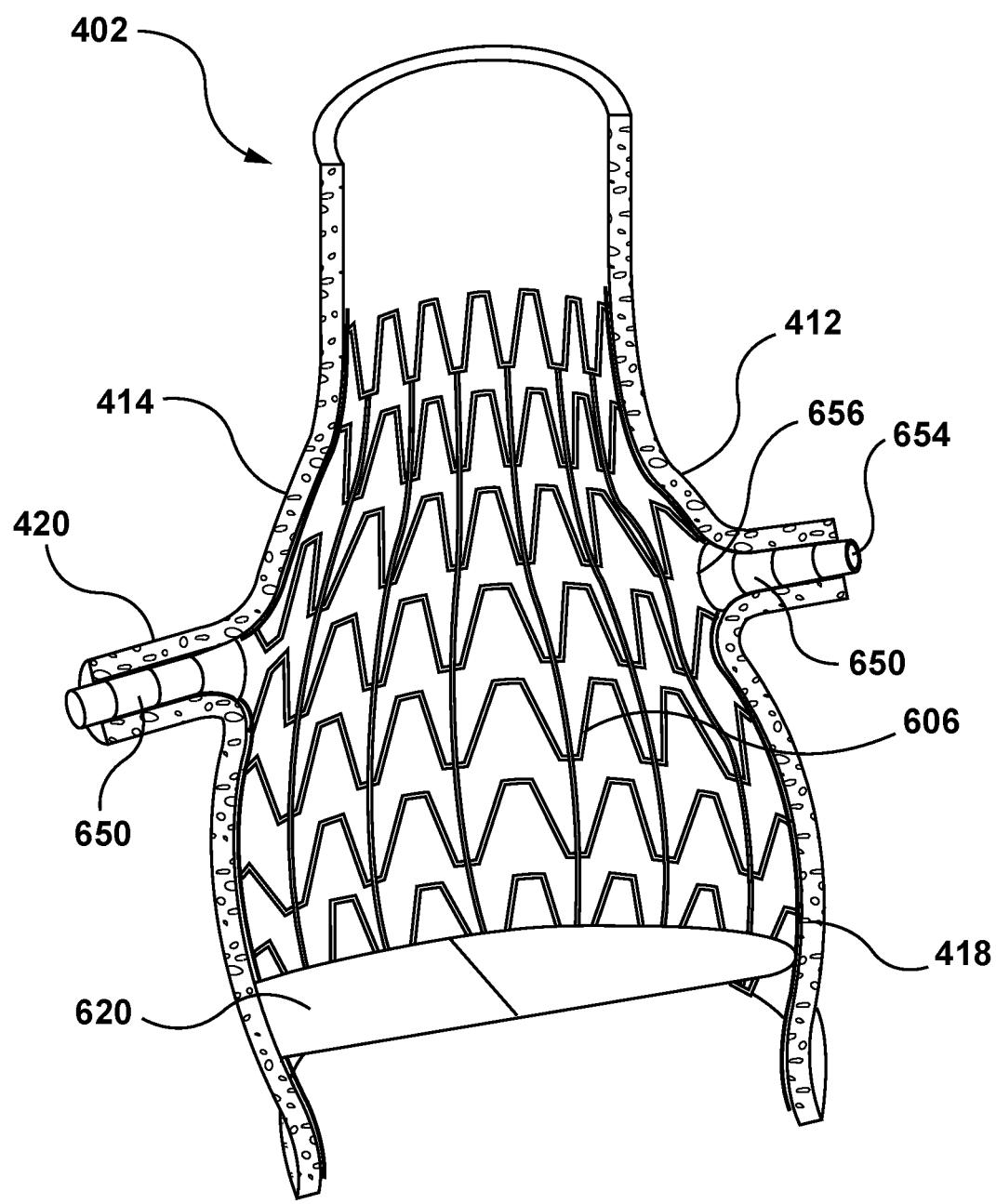

Valve assembly 600 is shown in a fully deployed configuration shown in FIG. 27. Valve assembly 600 with coronary arms 650 maintains blood flow to the coronary arteries. Further, coronary arms 650 provide support for frame 606 when coronary arms 650 are deployed in the coronary arteries. Thus, frame 606 is not required to provide as much radial force to maintain frame 606 at the desired location as compared to prosthetic valve assemblies without coronary arms 650. Further, coronary arms 650 provide access to the coronary arteries for future interventional procedures (e.g., balloon angioplasty, stent placement).

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment

What is claimed is:

1. A stent assembly having a radially compressed delivery configuration and a radially expanded deployed configuration, the stent assembly comprising:
a generally tubular frame having a first end and a second end, the frame defining a central passage and a central axis;
a secondary passage, defined between an inner surface of the frame and an outer surface of an inner rib closer to the central axis than the frame;
a proximal alignment arm, wherein the proximal alignment arm is coupled to the frame at the first end of the frame; and
a skirt coupled to the inner rib such that a coronary channel is defined between an outer surface of the skirt and the frame,
wherein the stent assembly does not include a prosthetic valve attached to the frame,
wherein the stent assembly is configured to be deployed within an aorta with the proximal alignment arm deployed in a sinus of an aortic valve, and
wherein with the stent assembly deployed in the aorta, the proximal alignment arm encircles an ostium of a coronary artery, and a coronary pocket is defined between the outer surface of the skirt and the aortic sinus in which the proximal alignment arm is disposed.

2. The stent assembly of claim 1, wherein the secondary passage is generally parallel with the central axis of the frame.

3. The stent assembly of claim 1, wherein the secondary passage comprises two secondary passages.

4. The stent assembly of claim 1, wherein the proximal alignment arm comprises two proximal alignment arms.

5. The stent assembly of claim 1, wherein the coronary channel is configured to rotationally align with an ostium of a coronary artery.

6. The stent assembly of claim 1, wherein when in the radially expanded deployed configuration, the coronary channel is in fluid communication with the coronary pocket and the coronary pocket is in fluid communication with the coronary artery.

7. A device comprising:
a generally tubular anchor stent having a radially compressed delivery configuration and a radially expanded deployed configuration, the anchor stent having a central longitudinal axis and including:
a central passage;
a secondary passage disposed radially outward of the central passage, the secondary passage being generally parallel to the central longitudinal axis; and a proximal alignment arm extending from a proximal terminal end of the anchor stent, the proximal alignment arm including a first end coupled to the anchor stent, a second end coupled to the anchor stent, and a middle portion forming a loop between the first end and the second end; and a valve component having a radially compressed delivery configuration and a radially expanded deployed configuration, the valve component being separate from the anchor stent prior to delivery to a treatment site, the valve component including:

a frame; and a prosthetic valve coupled to the frame, wherein with the anchor stent in the radially expanded deployed configuration, the valve component is configured to be delivered through the central passage of the anchor stent with the valve component in the radially compressed delivery configuration.

8. The device of claim 7, wherein the anchor stent is configured to be deployed in a native aorta, the valve component is configured to be deployed at a native aortic valve, and the secondary passage is configured to enable blood flow to an ostium of a native coronary artery.

9. The device of claim 7, wherein the secondary passage extends from a distal terminal end of the anchor stent to the proximal terminal end of the anchor stent.

* * * * *